United States Patent [19]
Enhsen et al.

[11] Patent Number: 5,559,258
[45] Date of Patent: Sep. 24, 1996

[54] ETHYLENICALLY UNSATURATED BILE ACID DERIVATIVES, PROCESSES FOR THEIR PREPARATION AND PRECURSORS

[75] Inventors: Alfons Enhsen, Büttelborn; Heiner Glombik, Hofheim am Taunus; Stefan Müllner, Hochheim am Main; Günther Wess, Erlensee, all of Germany

[73] Assignee: Hoechst Aktiengesellschaft, Frankfurt am Main, Germany

[21] Appl. No.: 345,803

[22] Filed: Nov. 22, 1994

Related U.S. Application Data

[63] Continuation of Ser. No. 993,243, Dec. 17, 1992, abandoned.

[30] Foreign Application Priority Data

Dec. 20, 1991 [DE] Germany .......................... 41 42 323.2
Sep. 1, 1992 [DE] Germany .......................... 42 29 033.3

[51] Int. Cl.$^6$ ...................................................... C07J 9/00
[52] U.S. Cl. .................. 552/550; 548/528; 552/521; 552/548; 552/549; 552/551; 552/552
[58] Field of Search .................................. 552/548, 549, 552/550, 551, 552, 521; 548/528

[56] References Cited

U.S. PATENT DOCUMENTS

| | | | |
|---|---|---|---|
| 3,383,281 | 5/1968 | Wolf et al. | 260/428 |
| 4,439,366 | 3/1984 | Scolastico et al. | 260/397.1 |
| 4,440,688 | 4/1984 | Scolastico et al. | 260/397.1 |
| 4,810,422 | 3/1989 | Hatono et al. | 260/397.1 |

FOREIGN PATENT DOCUMENTS

| | | |
|---|---|---|
| 0417725 | 9/1990 | European Pat. Off. . |
| 0489423 | 12/1991 | European Pat. Off. . |
| 4142379.8 | 12/1992 | Germany . |
| 59-046300 | 3/1984 | Japan . |
| 123341 | 7/1970 | New Zealand . |
| 235818 | 4/1988 | New Zealand . |
| 224377 | 4/1988 | New Zealand . |
| 230957 | 10/1989 | New Zealand . |
| 235285 | 9/1990 | New Zealand . |
| 235871 | 10/1990 | New Zealand . |

OTHER PUBLICATIONS

Hughes et al., "Formylation of Bile Acids," Journal of the Chemical Society, Part IV, pp. 3437–2438, 1949.
Wolf et al., "Intramolecular Catalysis. VI. Selectivity in 7,12-dihydroxy Steroids and Enhancement of 12 –Hydroxyl Reactivity by Substituents at Carbon 3," J. Org. Chem., vol. 38, No. 7, pp. 1276–1279, 1973.
Hilton et al., "The Synthesis and Antibacterial Activity of Some Basic derivatives of the Bile Acids," Journal of the Chemical Society, Part IV 3449–3453, 1955.
Levy et al., "The Action of Triphenylphosphine Dibromide on Sterol and Bile Acid Derivatives," The Journal of Organic Chemistry, vol. 30, No. 10, pp. 3469–3472, Oct. 1965.
Cayen, Pharmac. Ther. vol. 29, pp. 157–204, 1985.
Krause et al., Atherosclerosis VIII, G. Crepaldi et al., editors, Excerpta Medica, 1989, pp. 707–710.
Vaccaro et al., Atherosclerosis VIII, G. Crepaldi et al., editors, Excerpta Medica, 1989, pp. 605–608.
Reale, Attilio, Atherosclerosis VIII, G. Crepaldi et al., editors, Excerpta Medica, 1989, pp. 541–545.
Redel et al., Bulletin of the Chemical Society of France, pp. 877–883, 1949.
Jones et al., Journal of the Chemical Society, pp. 2164–2168, 1949.
Ahlheim et al., "Kondensationspolymerisation von Gallensauren," Makromol. Chem., Rapid Commun. vol. 9, pp. 299–302, 1988.
Chemical Abstracts, vol. 109, No. 38346 (1988).
Wess et al., "Modified Bile Acids: Preparation of 7α, 12α–dihydroxy–3β–and 7α, 12α–dihydroxy–3α–(2–hydroxyethoxy)–5β–cholanic acid and their biological activity," Tetrahedron Letters, vol. 33, No. 2, pp. 195–198, 1992.
Ahlheim et al., "Radikalisch polymerisierbare Gallensauren in Monoschichten Mitzellen und Vesikeln," Markromol. Chem. vol. 193, pp. 779–797 (1992).
Wei–Yuan Huang, "Synthesis of perfluoroalkyl–containing steroidal glycosides," Chinese Journal of Chemistry, vol. 10, No. 3, 1992.
Chemical Abstracts, vol. 101, No. 91353k, 1984.
Kritchevsky et al., 385 Steroids—Structure, Function and Regulation, vol. 47, No. 1, pp. 41–48, Jan. 1986.
Miyata et al. "Functional Monomers and Polymers, 26," Die Makromolekulare Chemie, 176, 2139–2142 (1975).
Mullner et al., "Synthesis of Affinity Chromatography and Electrophoresis Matrices for the Purification of Bile Acid Transport Proteins," Chromatographia, vol. 32, No. 5/6, pp. 265–268, Sep. 1991.
Ahlheim et al., "Bile Acids Bound to Polymers," Polymer Bulletin, vol. 15, pp. 497–501, 1986.

Primary Examiner—José G. Dees
Assistant Examiner—Barbara S. Frazier
Attorney, Agent, or Firm—Finnegan, Henderson, Farabow, Garrett & Dunner, L.L.P.

[57] ABSTRACT

Ethylenically unsaturated bile acid derivatives of the formula I $$G\text{—}X\text{—}A \qquad I$$

in which G, X and A have the meanings indicated, are described. They are suitable for the preparation of polymeric bile acid derivatives. Bile acid derivatives of the formula IVa $$G\text{—}X' \qquad IVa$$

in which G and X' have the meanings indicated, are also described. They are useful synthesis components for the preparation of pharmaceuticals.

9 Claims, No Drawings

ETHYLENICALLY UNSATURATED BILE ACID DERIVATIVES, PROCESSES FOR THEIR PREPARATION AND PRECURSORS

This application is a continuation of application Ser. No. 07/993,243, filed Dec. 17, 1992, now abandoned.

The invention relates to ethylenically unsaturated bile acid derivatives. They are suitable for the synthesis of bile acid polymers. The invention also relates to precursors which can be used as components for the synthesis of bile acid derivatives.

Bile acids have important physiological functions in fat digestion, for example as cofactors of pancreatic lipases and as natural detergents for the solubilization of fats and fat-soluble vitamins. As final products of the metabolism of cholesterol, they are synthesized in the liver, stored in the gall bladder and released from this by contraction into the small intestine, where they display their physiological action. The major part of the secreted bile acids is recovered again via the enterohepatic circulation.

Non-absorbable, insoluble, basic and crosslinked polymers have been known for a long time for binding bile acids and are used therapeutically as a result of these properties.

The bile acid derivatives according to the invention have a high affinity for the specific physiological bile acid transport systems in humans and animals. These compounds are thus able to inhibit the specific bile acid transport in a concentration-dependent manner, being transported poorly to not at all themselves. Surprisingly, it has now been found that polymeric bile acid derivatives prepared from the compounds according to the invention interact with the transport systems with retention or even with an increase in affinity. This makes them useful for use as non-systemic pharmaceuticals.

The invention relates to ethylenically unsaturated bile acid derivatives of the formula I $$G—X—A \qquad (I)$$

in which
G is a bile acid derivative,
X is a bridge group and
A is a polymerizable, ethylenically unsaturated group.

The compounds of the formula I are used as starting compounds for the preparation of polymeric bile acid derivatives.

Preferably, among the individual groups the following are understood as meaning:

G: a free bile acid or its alkali metal or alkaline earth metal salt or a bile acid esterified on ring D, which is bonded via ring A or B thereof, preferably via ring A, to the group X, to which the formula II applies $$M_o—(Z)_p \qquad (II)$$

in which
Y is adjacent to G and is

—O—, —NR'—, —OC—, —NR'—C—
       ‖       ‖
       O       O

Z is $(C_1-C_{12})$-alkylene or $(C_7-C_{13})$-aralkylene, where individual, preferably 1 to 4, methylene groups in the alkylene chain of the alkylene or aralkylene radical can be replaced by groups such as

—O—, —NR'—, —NR'C—, —O—C— or NR'C—NR"—
             ‖        ‖         ‖
             O        O         O preferably by groups of one type, and
o and p independently of one another are zero or 1, where o and p are not simultaneously zero
A:

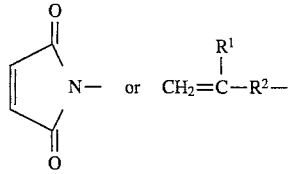

where
$R^1$ is hydrogen or $CH_3$ and
$R^2$ is

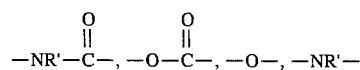

—NR'—C—, —O—C—, —O—, —NR'—
      ‖      ‖
      O      O or a single bond, where the carbonyl groups are adjacent to the C—C double bond, and
R' and R" independently of one another are hydrogen or $(C_1-C_6)$alkyl, preferably $(C_1-C_3)$alkyl.

Preferred compounds of the formula I are those in which G corresponds to the formula III

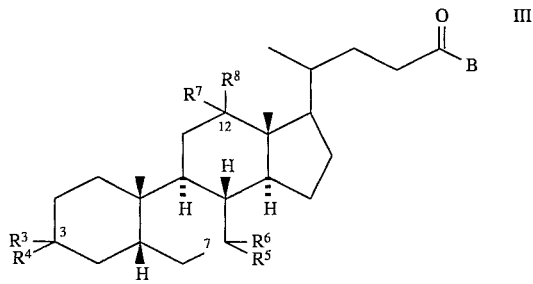

in which
$R^3$ to $R^8$ independently of one another are hydrogen, OH, $NH_2$ or an OH group protected by an OH protective group and one of the radicals $R^3$, $R^4$, $R^5$ and $R^6$ is a bond to the group X, where this bond starts from positions 3($R^3$ or $R^4$), preferably 3β, or 7 ($R^5$ or $R^6$) and the other position 7 or 3 in each case carries an OH group or a protected OH group, B is —OH, —O-alkali metal, —O-alkaline earth metal, —O—$(C_1-C_{12})$-alkyl, —O-allyl or —O-benzyl, preferably —OH, —O-alkali metal or —O—$(C_1-C_6$-alkyl, —O-allyl or —O-benzyl, where a resultant ester group

is an ester which can be hydrolyzed by acid or by base,
Y is —O—, —NR'—,

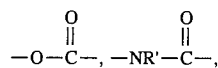

—O—C—, —NR'—C—,
    ‖        ‖
    O        O

Z is $(C_1-C_{12})$-alkylene, $(C_7-C_{13})$-aralkylene, where 1 to 3 methylene groups in the alkylene chain are replaced by the groups —O—, —NR'—,

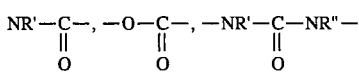

and o and p independently of one another are zero or 1, but not simultaneously zero.

A is

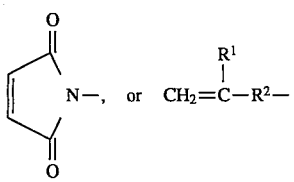

where
R¹ is hydrogen or CH₃ and
R² is

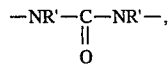

or a single bond, in which
R' and R" independently of one another are hydrogen or (C₁–C₆)-alkyl.

If p=zero and o=1 applies, Y is preferably

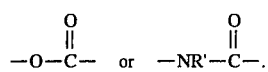

If p=1 and o=o applies, Z is preferably (C₁–C₁₂)-alkylene, where 1–3 methylene groups are replaced by

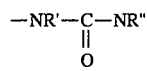

If p=1 and o=1 applies, Y is preferably —O—, among these, it is preferred that Z is (C₁–C₁₂)-alkylene or (C₇–C₁₃)-aralkylene, where 1 or 2 methylene groups, preferably a methylene group, are replaced by

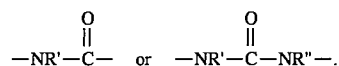

It is furthermore preferred here that a methylene group of Z is

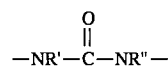

if Z itself is an aralkylene radical, in which the aryl radical is meta-linked, Z on the one hand carries a group

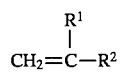

as radical A, in which R² is a single bond, and on the other hand carries an

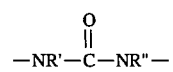

group which is meta-linked to the aralkylene radical via a methylene group.

It is likewise preferred here that, if Z is a (C₁–C₁₂)-alkylene group, at most one methylene group is replaced by

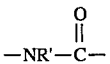

and as radical A

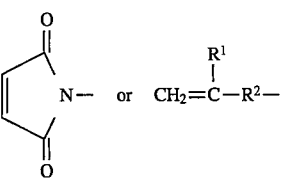

applies, R² being

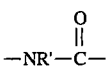

If R² is a single bond and o=0 and p=1, Z is preferably (C₁–C₃)-alkylene.

It is furthermore particularly preferred that Y is not directly adjacent to the group replacing a methylene group of Z, and is also not adjacent to

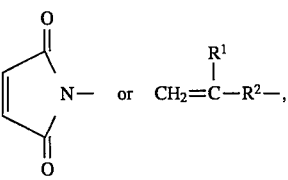

if R² is a single bond.

In the above and the following embodiments, "alkyl" is understood as meaning a straight-chain or branched alkyl radical.

OH protective groups are understood as meaning:
An alkyl radical having 1–10 carbon atoms or alkylene radical having 2 to 10 carbon atoms and which is branched or unbranched,
a cycloalkyl radical having 3–8 carbon atoms,
a phenyl radical which is unsubstituted or substituted 1–3 times by F, Cl, Br, (C₁–C₄)-alkyl or (C₁–C₄)alkoxy,
a benzyl radical which is unsubstituted or substituted 1–3 times by F, Cl, Br, (C₁–C₄)-alkoxy or a

radical, where R'" is hydrogen or (C₁–C₄)-alkyl.

The said bile acid derivatives according to the invention are used for the preparation of polymeric bile acid derivatives. Polymeric bile acid derivatives, their preparation and use are described in German patent application P 4142379.8. The polymeric bile acid derivatives have a high affinity for the bile acid transport system of various organs, but are not transported themselves on account of their size and their molecular weight. With the aid of the bile acid derivatives according to the invention or polymeric bile acid derivatives physiological bile acid transport can therefore be specifically inhibited. This is in particular of importance for the inhibition of bile acid reabsorption in the small intestine, since this leads in humans and animals to a proven extent to a reduction in the serum cholesterol level. The polymeric bile acid derivatives which can be prepared from the compounds of the formula I according to the invention are therefore useful pharmaceuticals, in particular hypolipidemics.

Depending on the particular functional groups, the compounds according to the invention are prepared according to synthesis principles 1) to 9). The last step usually comprises the insertion of the group A in compounds of the formula IV

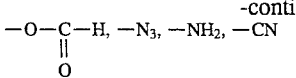 (IV)

in which G has the meaning indicated for formula I and X' is a bridge group as indicated for formula I, which additionally contains a reactive radical which enables the introduction of A.

Compounds of the formula IVa

G—X' (IVa)

in which
G is a bile acid radical of the formula V

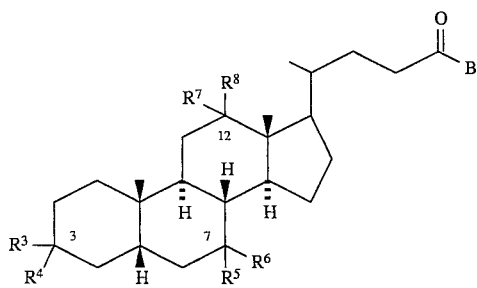

in which one of the radicals $R^3$ to $R^6$ has the meaning of X' and the other radicals $R^3$ to $R^8$ independently of one another are hydrogen, OH or a protected OH group B is —OH, —O-alkali metal, —O-alkaline earth metal, —O—($C_1$–$C_{12}$)-alkyl, —O-allyl or —O-benzyl, preferably —OH, —O-alkali metal or —O—($C_1$–$C_6$)-alkyl, —O-allyl or —O-benzyl,
and
X' is a radical of the formula VI

Y'—Z' (VI)

in which
Y' is adjacent to G and is a single bond,

—O—$(CH_2)_{2-12}$—,
—$(CH_2)_{1-6}$— or
—NH—C—$(CH_2)_{2-6}$—
   ‖
   O

Z' is

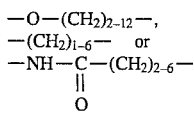

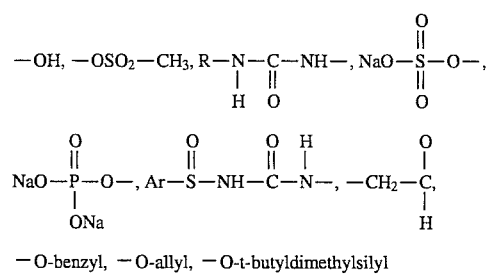

—O-benzyl, —O-allyl, —O-t-butyldimethylsilyl

-continued
—O—C—H, —$N_3$, —$NH_2$, —CN
   ‖
   O or bromine are new. The invention therefore also relates to the compounds of the formula IVa.

Ar is a phenyl radical which is unsubstituted or substituted 1 to 2 times by F, Cl, Br, ($C_1$–$C_4$)-alkyl or ($C_1$–$C_4$)-alkoxy, R is ($C_1$–$C_4$)-alkyl or Ar.

The compounds IVa according to the invention are useful synthesis components for the preparation of pharmaceuticals (cf. for example, EP-A-0,489,423) and the compounds of the formula I. They can be employed in the synthesis of pharmaceuticals as such or after conversion of Z into another reactive group, such as, for example, from $N_3$ to $NH_2$.

Synthesis principles (explained in examples in which G is a radical of the formula III):

1) Compounds of the formula I, in which Y is —O—, Z is alkylene or aralkylene, A is

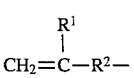

and a free acid, its salt or an ester which can be hydrolyzed a free acid, its salt or an ester which can be hydrolyzed

by base, are obtained, for example, by the following reaction sequence from compounds (1) which are in some cases described in EP-A-0,489,423. In this process, compounds (1) are converted by reactions with α, ω-alkanediols, (alkane=2–12 carbon atoms) with addition of base (for example pyridine, triethylamine or KOH) at temperatures of 60° to 140° C. into chain-extended bile acid derivatives of the formula (2), for example, in the case of conversion with 1,6-hexanediol (6 carbon atoms), the reaction is carried out in an excess of pyridine without further solvent and at temperatures of 100° C. Protective groups for the other OH groups in the bile acid molecule are not necessary in this case.

Compounds of the formula (3) are obtained by acid-catalyzed esterification of the —COOH function from compound (2) using an excess of methanol with exclusion of water. Esters of higher alcohols which can be hydrolyzed by base can likewise be prepared. The following alcohols are mentioned in particular: ethanol, i-propanol n-propanol, n-butanol. Numerous acids can be employed here as catalysts, for example $BF_3$, molecular sieve for water removal and hydrohalic acids. Preferably, HCl is used, which can also be produced in situ from organic acid chlorides, R˙COCl(R˙=$CH_3$, $C_2H_5$, $C_3H_7$). The reaction temperature in this case is between 0° and 30° C.

Compounds of the formula (4) are obtained by reaction of compound (3) with methanesulfonyl chloride in an excess of an organic base, preferably pyridine, at temperatures from −10° to 0° C. (with cooling). The solvents used in this case can be inert solvents, in particular dichloromethane.

The azides (5) are prepared by reaction of compound (4) with alkali metal azides, preferably Na azide in an aprotic solvent, for example DMF, at temperatures from 20° to 100° C. These azides can be reduced to the amines (6) by means of a catalyst, preferably at room temperature. Examples of catalysts which can be used are: Pd on carbon, Rh on alumina or Raney nickel. The preferred solvents are ethyl acetate, methanol or THF. If a moderately active catalyst (for example Pd/C with water) and a low hydrogen pressure (for example 1–5 bar) are chosen, the nitrile IVa (6a) can be isolated first, and can in turn be further reduced under more drastic conditions (preferably Rh on Al$_2$O$_3$: pressure (H$_2$)= 30–100 bar) to compound (6).

Amines of the formula (6) can be reacted to give polymerizable acrylates of the formula (I) (7), by coupling them with activated derivatives of acrylic acid. For example, the unsaturated acid chloride can be reacted between 0° and −20° C. in inert solvents, such as dichloromethane, preferably with the addition of bases such as pyridine, triethylamine, lutidine etc. Other amide formation methods of peptide chemistry can also be used, for example acid activation with ethyl 1,2-dihydro-2-ethoxyquinoline-1-carboxylate (EEDQ) in ethyl acetate, THF or the like, at temperatures between room temperature and reflux temperature. If heating is carried out for a relatively long time, addition of hydroquinone has a yield-increasing effect.

The reactions described above are summarized in reaction scheme 1.

Reaction scheme 1

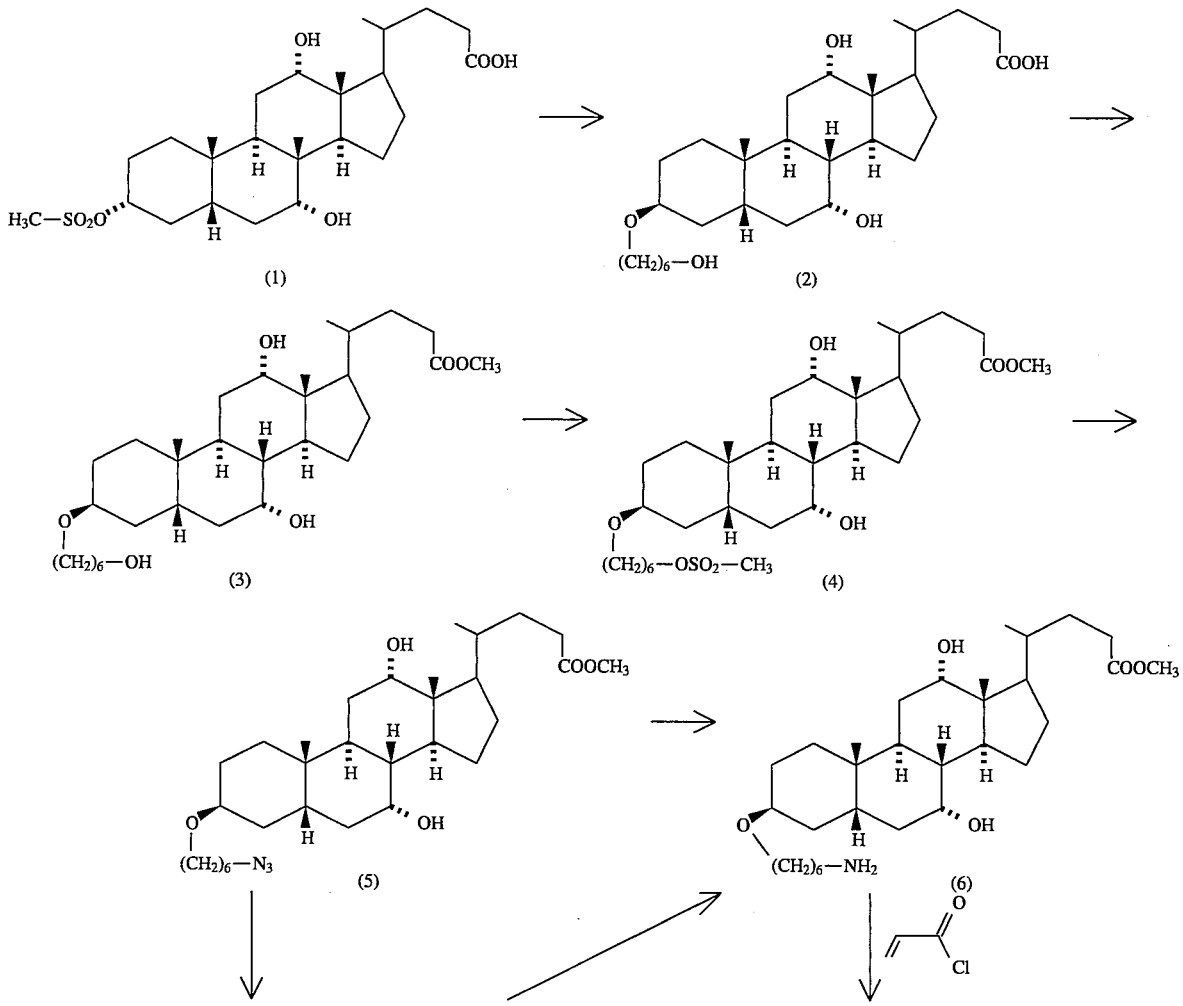

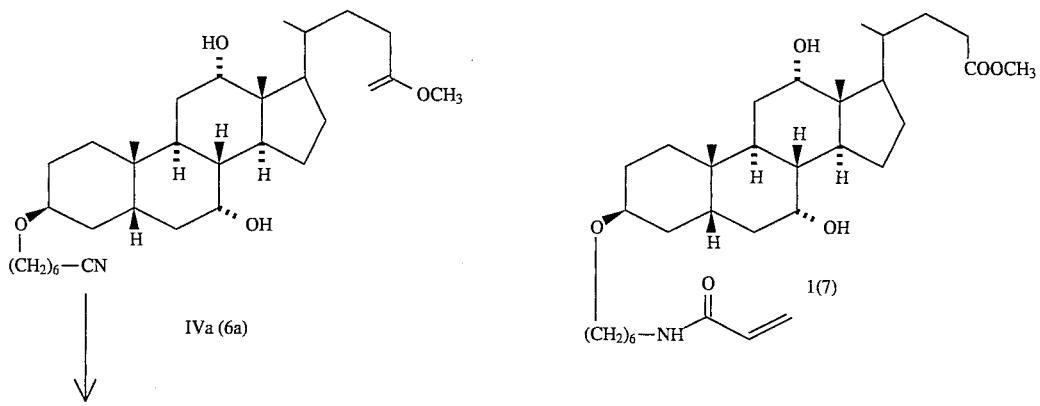

2) Compounds of the formula I in which Y is —O— and Z is alkylene or aralkylene, where 1–3 methylene groups are replaced by groups such as

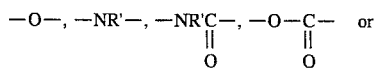

or (8), compound (8) being known from EP-A-0,489,423, after activation of the acid function of (9), preferably using EEDQ or using dicyclohexylcarbodiimide (DCC)/hydroxybenzotriazole (HOBT), for example in THF at 0° to 10° C. The reactions described can be carried out either with the preferred 3β-bile acid derivatives or with the corresponding 3α-analogs.

The reaction described is summarized in reaction scheme 2.

Reaction scheme 2:

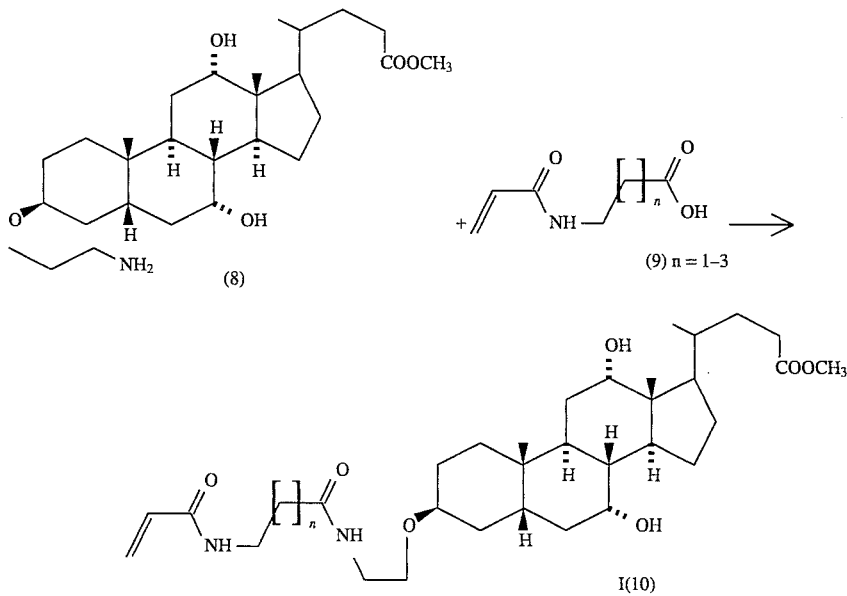

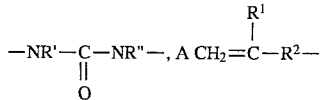

and and a free acid, its salt, or an ester which can be hydrolyzed by base, can be prepared as follows:

Polymerizable bile acid derivatives of the formula I (10) are obtained by linkage of the compound (9), which is known from the literature, for example with the amines (6)

3) Compounds of the formula I, in which o=zero and Z=alkylene or aralkylene, where 1–3 methylene groups are replaced by

A is

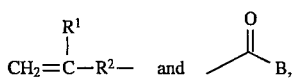

a free acid, its salt or an ester which can be hydrolyzed by base, can be prepared as follows:

Amines of the formula (15), which are used as starting compounds for polymerizable monomers I (16), are obtained from the ketones (11), which are known from the literature, by a Wittig-Horner Reaction using cyanomethyl phosphonates of the formula (12) with the addition of strong bases. The solvents used can be aprotic or protic, non-aqueous solvents. The reaction temperature is between room temperature and 70° C., preferably between 30° and 40° C. The bases used can be alkali metal hydroxides, preferably alkali metal hydrides or alkali metal alkoxides. By use of $NaOCH_3$ in methanol, transesterification of the bile acid methyl ester (11) which occurs as a side reaction is suppressed.

The nitriles IVa (13) thus obtained can be reduced in one or two steps (via IVa (14)) to the amines IVa (15). Depending on the reaction conditions used, 3α/β-stereoisomer mixtures are obtained, in which one isomer can predominate to a varying extent. A high selectivity of 3α:3β>90:10 can be achieved if the C—C double bond is first hydrogenated at moderate elevated pressures of 1–5 bar using Pd/C as the catalyst and the nitrile group is then reduced by means of Rh on $Al_2O_3$ at 30–50 bar. Chromatographic separation of the diasteromers can be achieved, for example, in the amine step. The amines IVa (15) are in turn reacted using (peptide chemistry) amide formation methods to give the monomeric bile acid derivatives I (16) (for example EEDQ method or DCC/HOBT method, for both see above). Both the use of the compound 9 and the introduction of α, ω-diols of medium chain length as in the compound 2 enable compounds of the type I (16) to be prepared.

The reactions described above are summarized in reaction scheme 3.

Reaction scheme 3

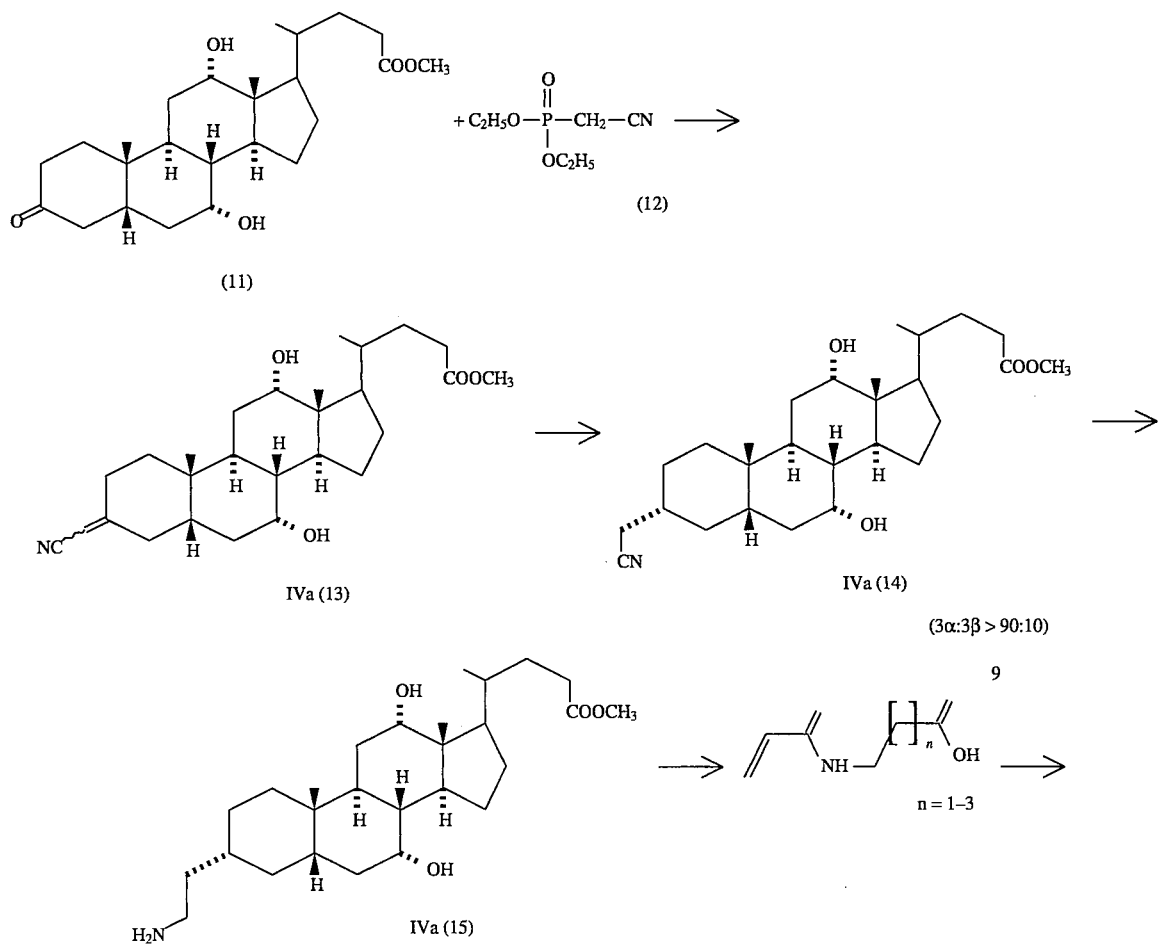

-continued
Reaction scheme 3

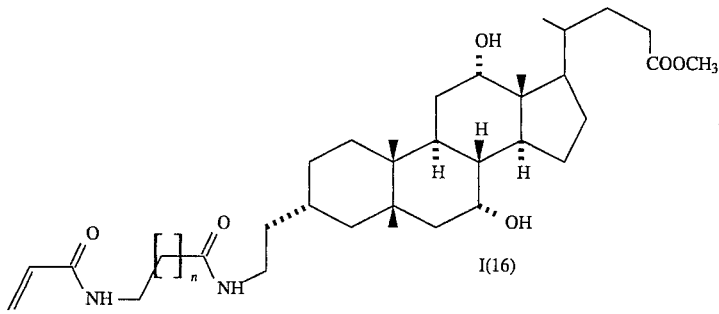

4) As in formula III, the bile acid derivative G can be present either as the free acid (B=OH), as the alkali metal salt (B=O-alkali metal) or as the ester (B=O—$C_1$-$C_{12}$-alkyl, O-allyl or O-benzyl). In the following, the preparation of esters and their hydrolysis is described. It is advantageous here in certain circumstances to protect OH groups by introduction of protective groups.

The preparation of the methyl esters which can be hydrolyzed by base is already described under 2) (compound (3) from compound (2)). The higher alkyl esters can also be prepared in the same way. For example, compound (II) is reacted with ethanol, n-propanol, i-propanol or n-butanol to give the corresponding esters. In the following, the preparation of preferably acidic hydrolyzable esters (for example tert-butyl esters) is described:

Bile acid derivatives known from the literature, of the formula (17), whose OH groups are protected by formyl, are reacted with thionyl chloride or preferably oxalyl chloride in inert solvents such as toluene and benzene at temperatures between 20° and 80° C. to give the corresponding acid chlorides, and the latter are converted into the tert-butyl esters (18) with the addition of tert-butyl alcohol with addition of base (pyridine or triethylamine) in inert solvents, such as dichloromethane at −20° to 0° C. By brief treatement with dilute alkali metal hydroxide solutions in solvents such as dioxane or THF, preferably at 60°–80° C., the formyl protective groups are removed again without hydrolysis of the tert-butyl ester function taking place (compound (IVa (19)). The process can likewise be used for the preparation of the 3-oxo-derivative of the formulae (21) and (22) from the known compound (20). The reaction described in summarized in reaction scheme 4a

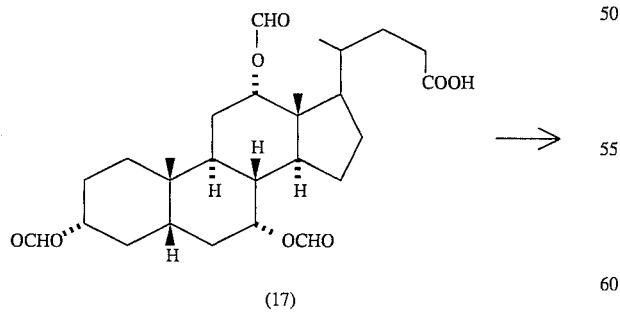

(17)

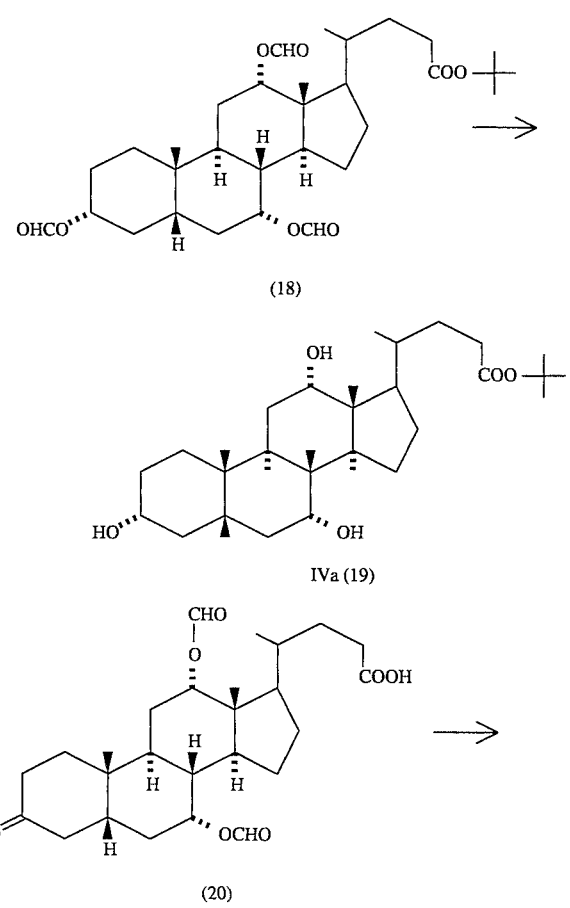

(18)

IVa (19)

(20)

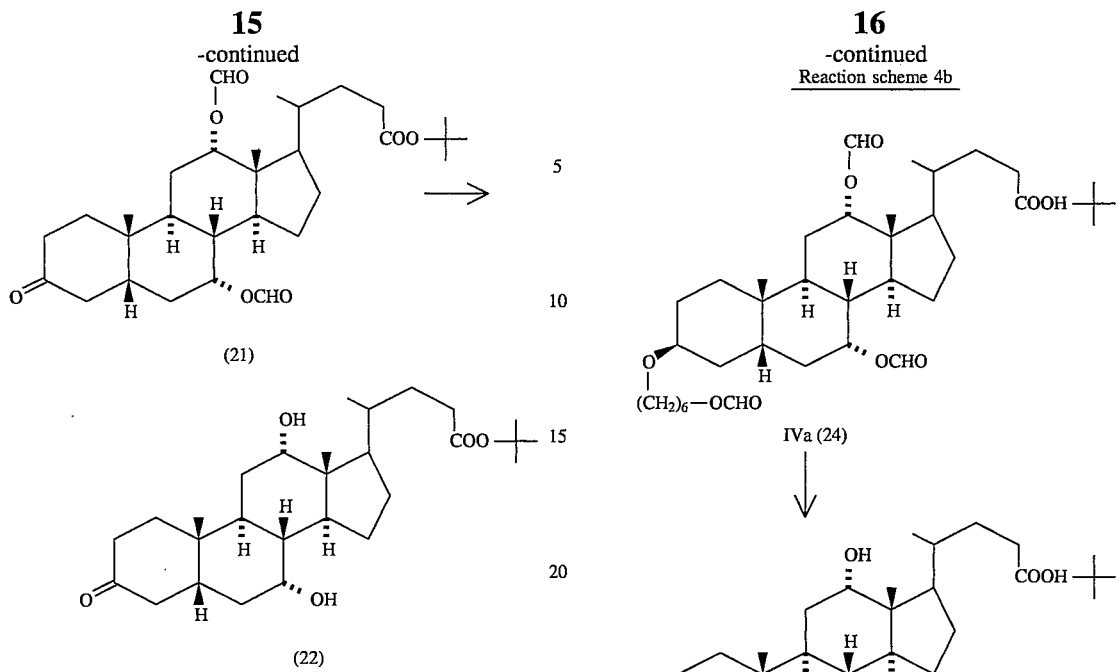

Process 4a described above can also be used for the esterification of primary alcohols chain-extended in the 3-position, for example of the formula (2). The introduction of the formyl protective groups is carried out by customary methods (HCOOH, HClO$_4$). Compound IVa (23), for example, is obtained and reacted to give the compounds IVa (24) and IVa (25) (cf. reaction scheme 4b).

Reaction scheme 4b

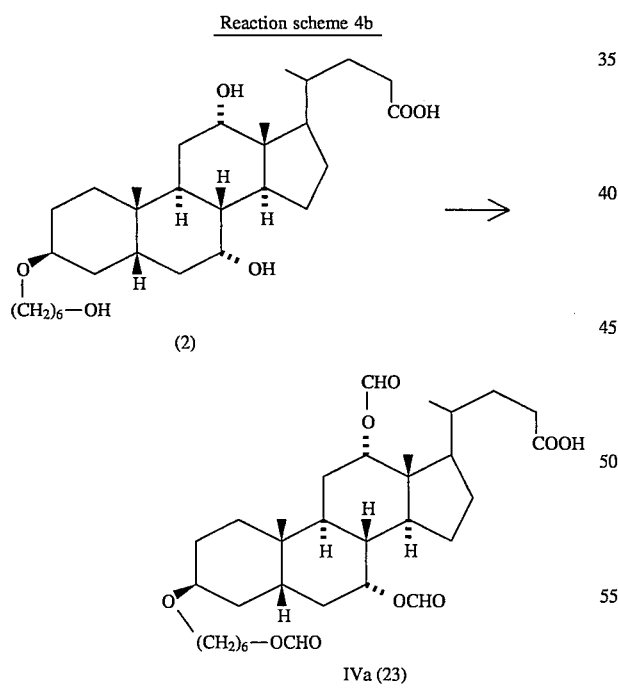

Like the methyl esters (3) and (11), the butyl esters IVa (24) and (23) can be used for the preparation of the bile acid derivatives of the formula I according to the invention.

5) Compounds of the formula I in which Y=—O— and Z=alkylene or aralkylene, A is

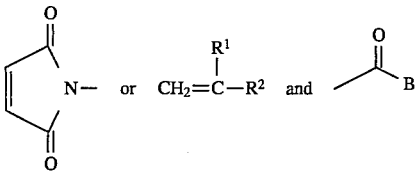

is a free acid, its salt or an ester which can he hydrolyzed by base, can he prepared as follows:

For example, the allyl ester IVa (26) can be prepared using a large excess of allyl alcohol and without further solvent in the presence of a catalyst, such as, for example, tetraethoxytitanium. The transesterification is preferably carried out at 60°–100°.

In the same way, the benzyl ester IVa (27) can be prepared from the methyl ester (8) using benzyl alcohol. The reaction proceeds readily with primary and secondary alcohols, but only poorly with tertiary alcohols. The esters thus accessible have differing properties, for example varying stability to bases during hydrolysis; some can be cleaved in the neutral range and others under hydrogenolytic conditions. The reaction described is summarized in reaction scheme 5a:

Reaction scheme 5a

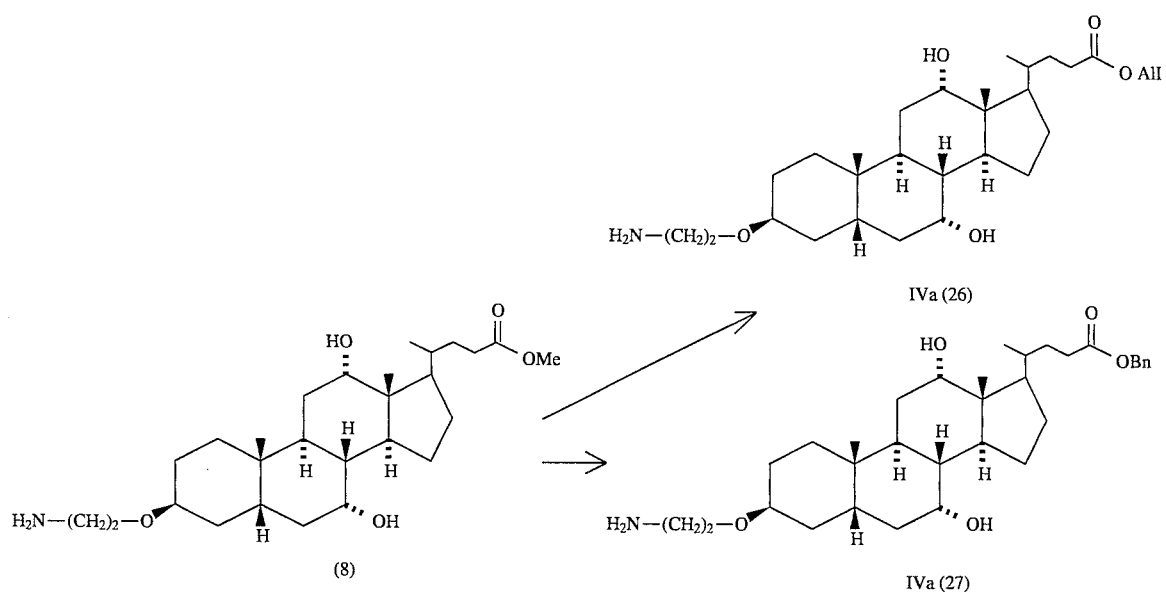

Polymerizable groups can be introduced into modified bile acid derivatives via the amino function. For example, the cyclic maleimides I (28) or I (29) can be prepared from the amino groups of the compounds (8) or IVa (27) using maleic anhydride under acidic conditions, for example in the presence of acetic acid, and at elevated temperatures.

A further possibility for introducing polymerizable groups consists in the reaction of the amino functions to give acrylamides. For this purpose, an activated acrylic acid derivative (acid chloride, mixed anhydride or active ester) is reacted with an amino function in the presence of a base (for example pyridine or triethylamine). Solvents such as dichloromethane, DMF or THF and temperatures from −20° to +50° C. are suitable for the reaction. Compound I (30) can be prepared from (8) and acryloyl chloride by this process. The basic hydrolysis of the methyl ester leads to the free acid I (31).

The reaction described is summarized in reaction scheme 5b:

Reaction scheme 5b

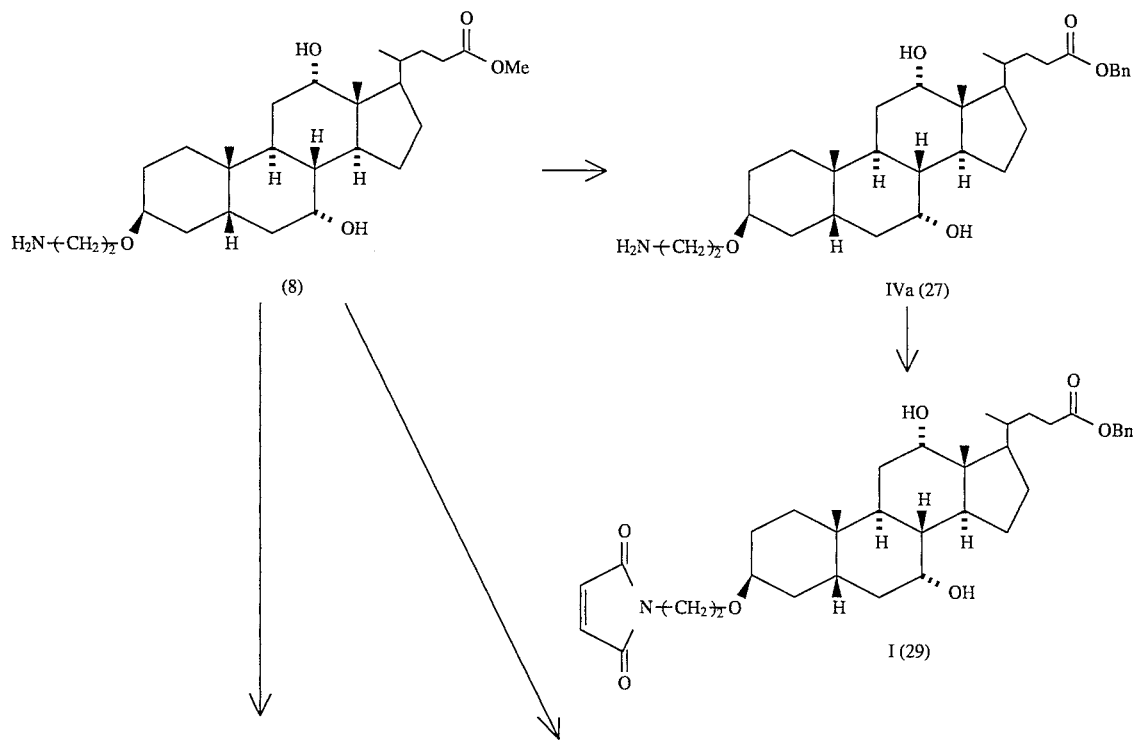

-continued
Reaction scheme 5b

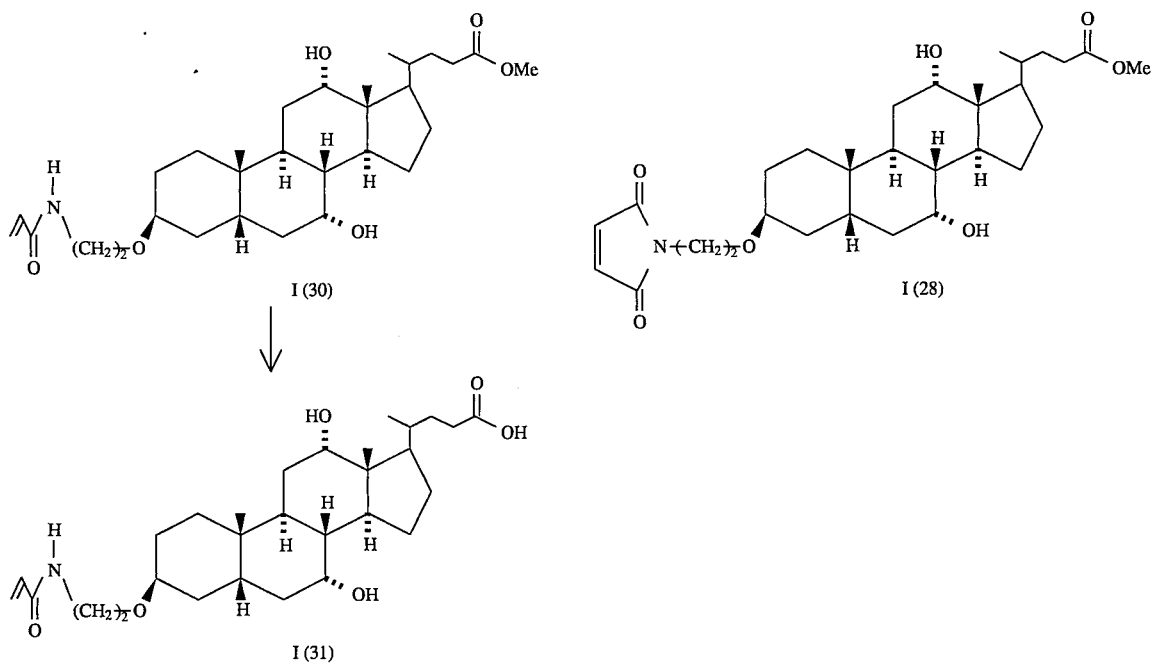

6) Compounds of the formula, I in which

is an ester which can be cleaved under acidic conditions, are prepared as follows:

for example: compound (32), in which Y is —O— and Z is alkylene, can be reacted to give compound I (41), in which A is

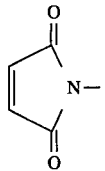

Compound (32) is selectively silylated on the primary hydroxyl group, for example using t-butyldimethyl silyl chloride (=TBDNS) or t-butyldiphenylsilyl chloride in dichloromethane, trichloromethane, tetrahydrofuran or dimethylformamide in the presence of a base (for example imidazole or triethylamine), at temperatures from −20° to 40° C. The hydrolysis of (33) under basic conditions leads to the free acid IVa (34). The t-butyl ester IVa (35) can be obtained from this after activation of the carboxyl group, for example as the active ester, mixed anhydride or alternatively acid chloride, and reaction with t-butanol.

The silyl protective group of the compound IVa (35) can be selectively set free using tetrabutylammonium fluoride in a suitable solvent (for example tetrahydrofuran, ether or dichloromethane). The primary alcohol function of the derivative IVa (36) thus obtained can be converted, as described (mesylation to give IVa (37), subsequent azide exchange to give IVa (38) and reduction to give IVa (39)) into the amino function of the compound IVa (39). As from (8) and IVa (27), a maleimide can be prepared from the amine IVa (39).

By hydrolysis of the t-butyl ester I (40) under acidic conditions (for example in trifluoroacetic acid or in trifluoroacetic acid/water mixtures, compound I (41) is obtained.

The reactions described above are summarized in reaction scheme 6a.

Reaction scheme 6a
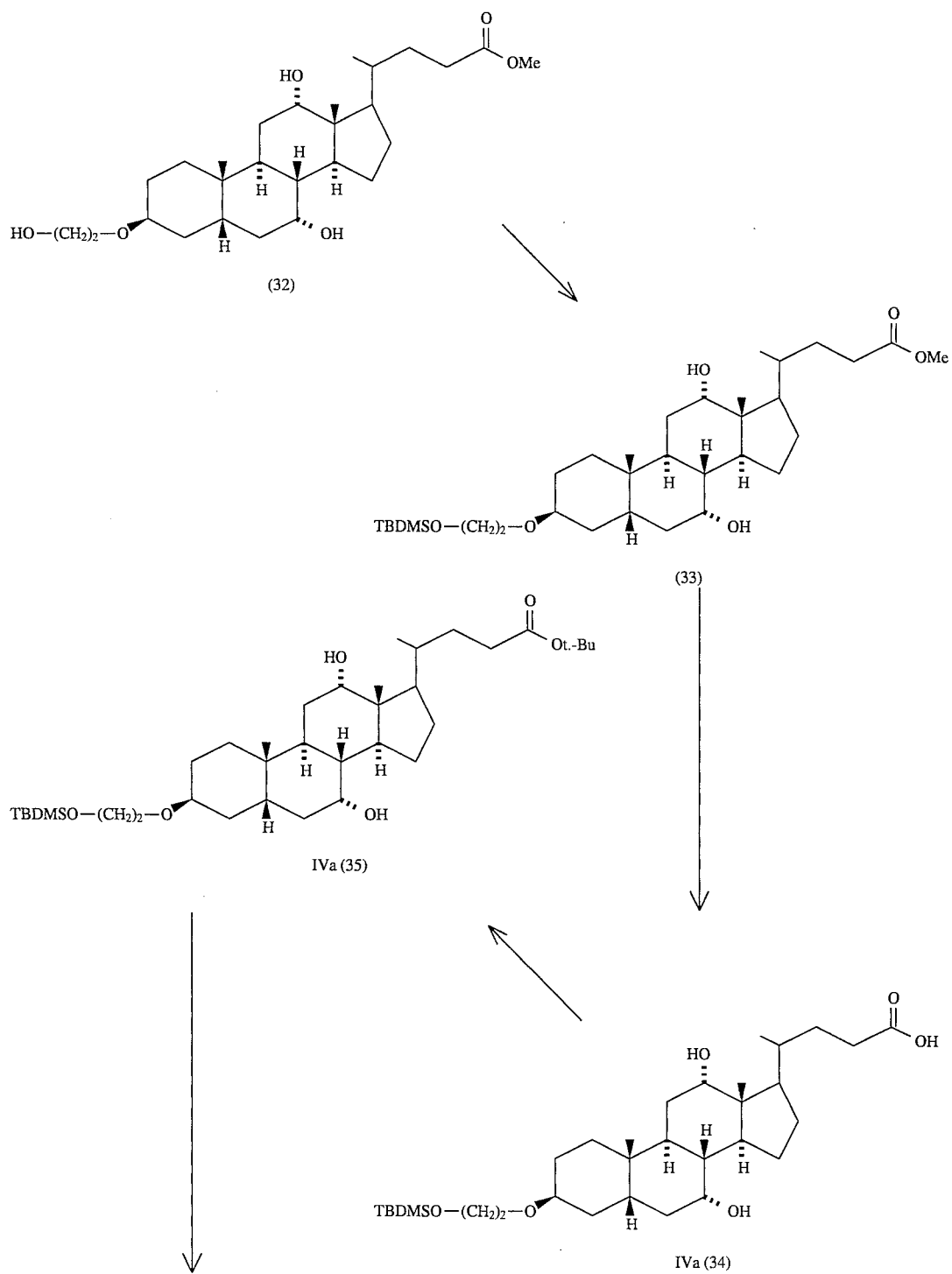

-continued
Reaction scheme 6a
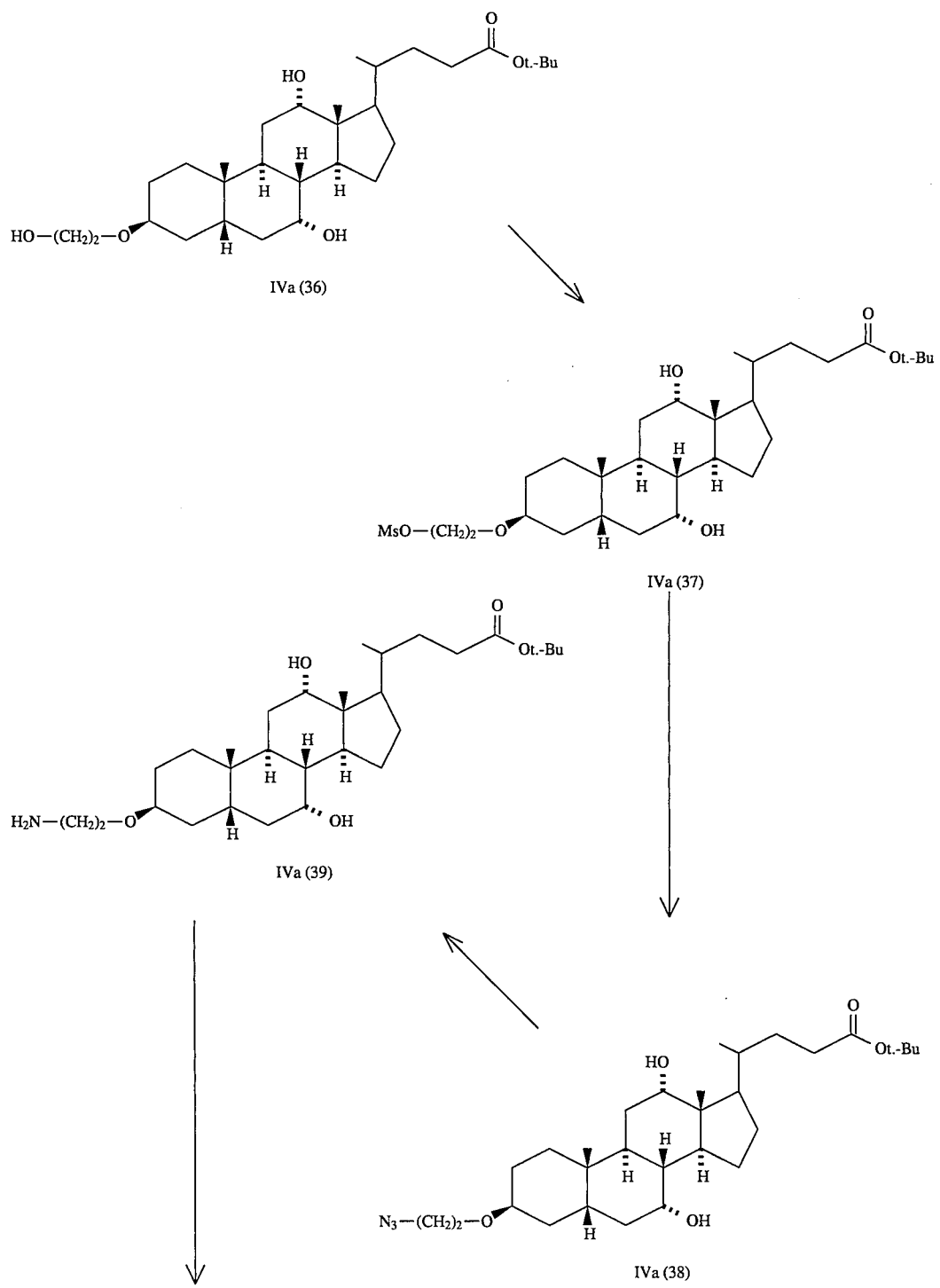

-continued
Reaction scheme 6a

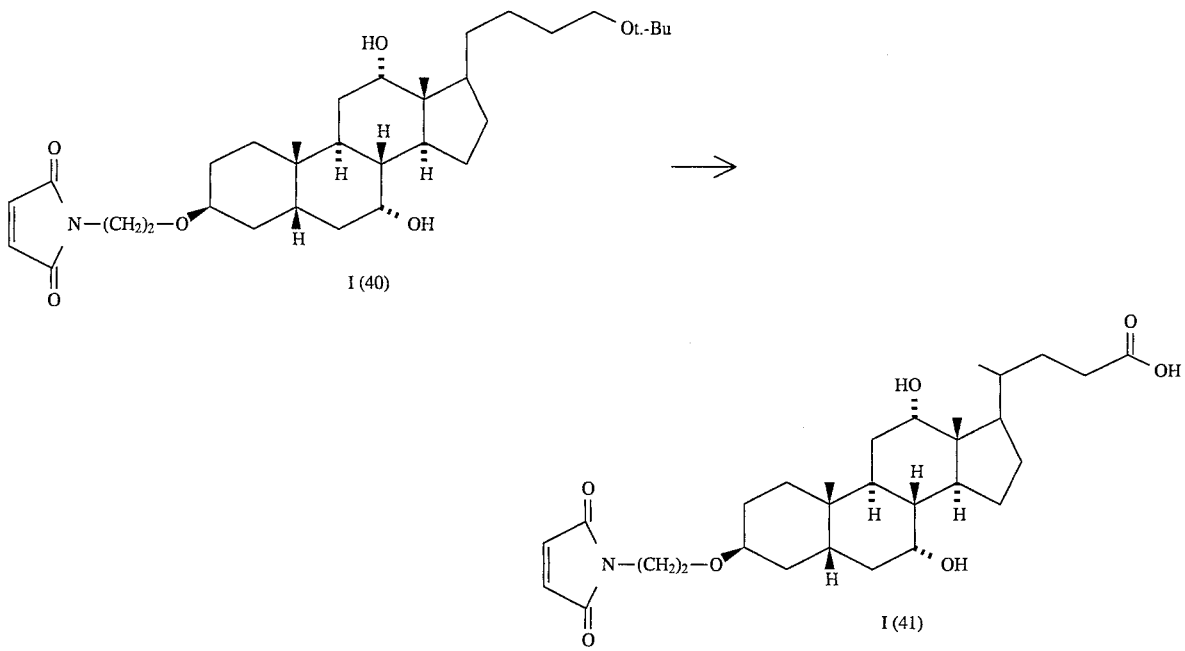

Likewise, compound (42), in which Y is —O— and Z is alkylene or aralkylene, can be reacted to give compound

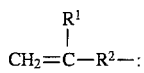

Compound (42) can be benzylated selectively with benzyl bromide in the presence of a suitable base (triethylamine or Hünig base) without further solvent at elevated temperature, from 70° to 130° C. The compound IVa (43) thus obtained can be converted into the t-butyl ester IVa (45) analogously to the reaction sequence (33) to IVa (35). The benzyl ether function of compounds of the type IVa (45) is cleaved to give alcohols such as the compound IVa (46) using hydrogen at a pressure of 1–5 bar in the presence of a catalyst such as, for example palladium on carbon, palladium or platinum in a suitable solvent such as, for example, methanol, ethyl acetate or tetrahydrofuran. Alcohols of the type IVa (46) can be converted by the processes already described (compounds IVa (36) to IVa (39), or (3) to (6)) into amino derivatives such as, for example, compound IVa (47). By reaction with suitable activated acrylic acid derivatives, acrylamides of the type I (48) are obtained.

The reaction sequence is summarized in reaction scheme 6b.

Reaction scheme 6b

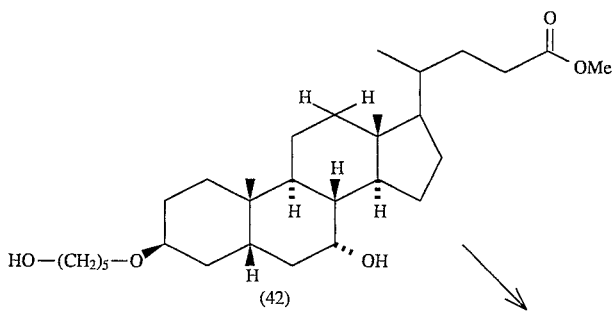

-continued
Reaction scheme 6b
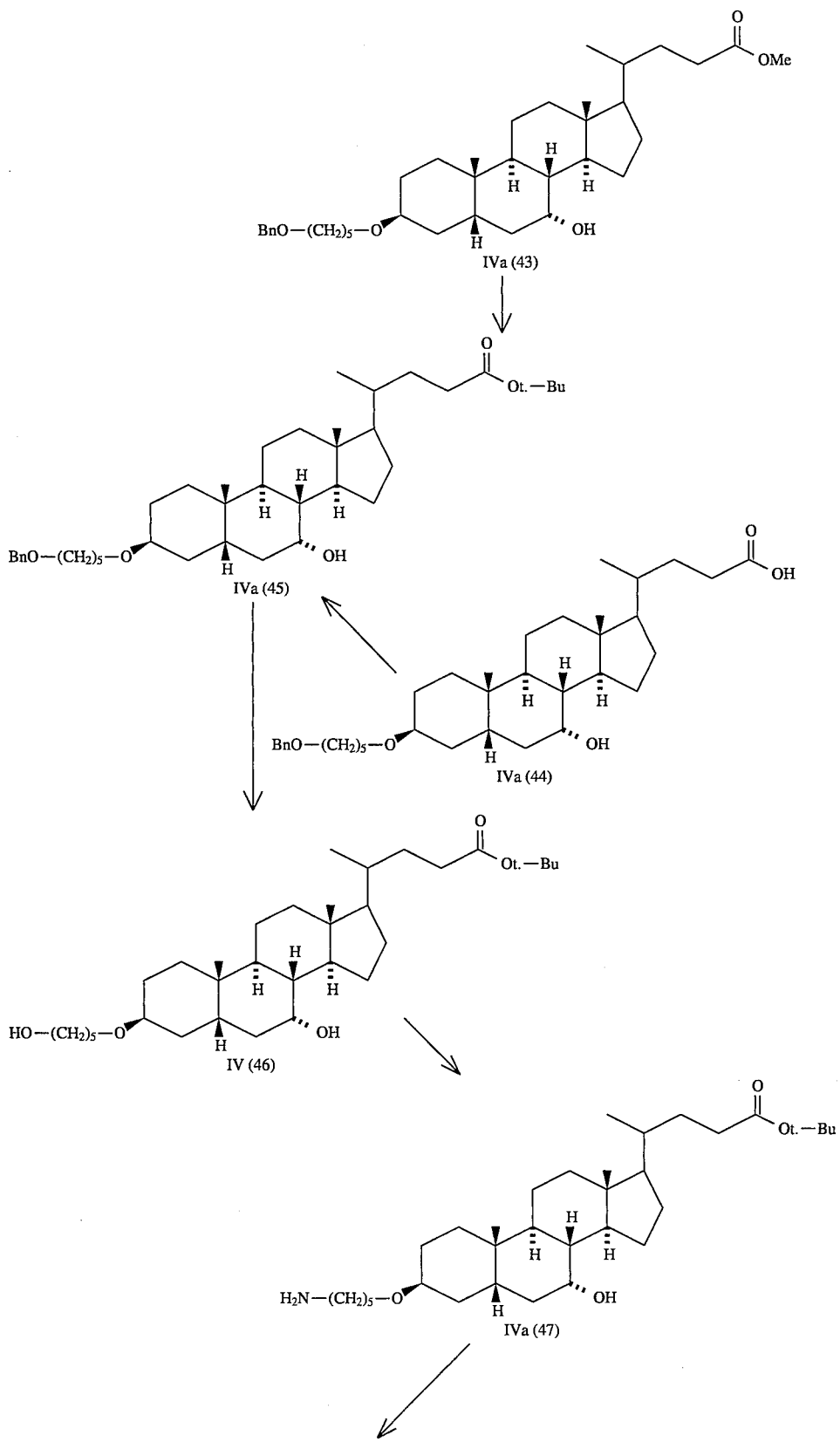

-continued
Reaction scheme 6b

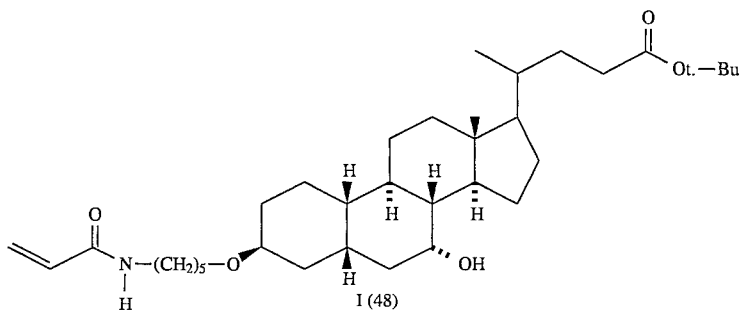

7) Compounds of the formula I in which Y is

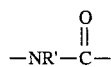

and A is

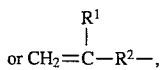

can be prepared as follows:

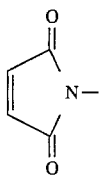

For direct linkage of the acrylic acid, the amine (49) can be reacted with an activated acrylic acid by the processes already described to obtain products of the type I(50). To introduce the radical X, activated forms of ω-halocarboxylic acids, such as, for example, 6-bromo-hexanoyl chloride, can be reacted with the amine (49) under the same abovementioned conditions to give compounds of the type IVa (51). By means of nucleophilic substitution, the halogen atom is replaced with alkali metal azides, such as sodium azide, in dimethylformamide or dimethyl sulfoxide at temperatures from 70° to 130° C.

The resulting azido compounds of the type IVa (52) are reduced to give amines, either by hydrogenation with hydrogen in the presence of a catalyst (palladium on carbon, platinum or Raney nickel) or by reaction with tributylphosphine or triphenylphosphine at room temperature in a suitable solvent such as tetrahydrofuran. The acrylamide I (54) can be prepared from the amine IVa (53) by the process described for I (50).

The reactions described are summarized in reaction scheme 7.

Reaction scheme 7

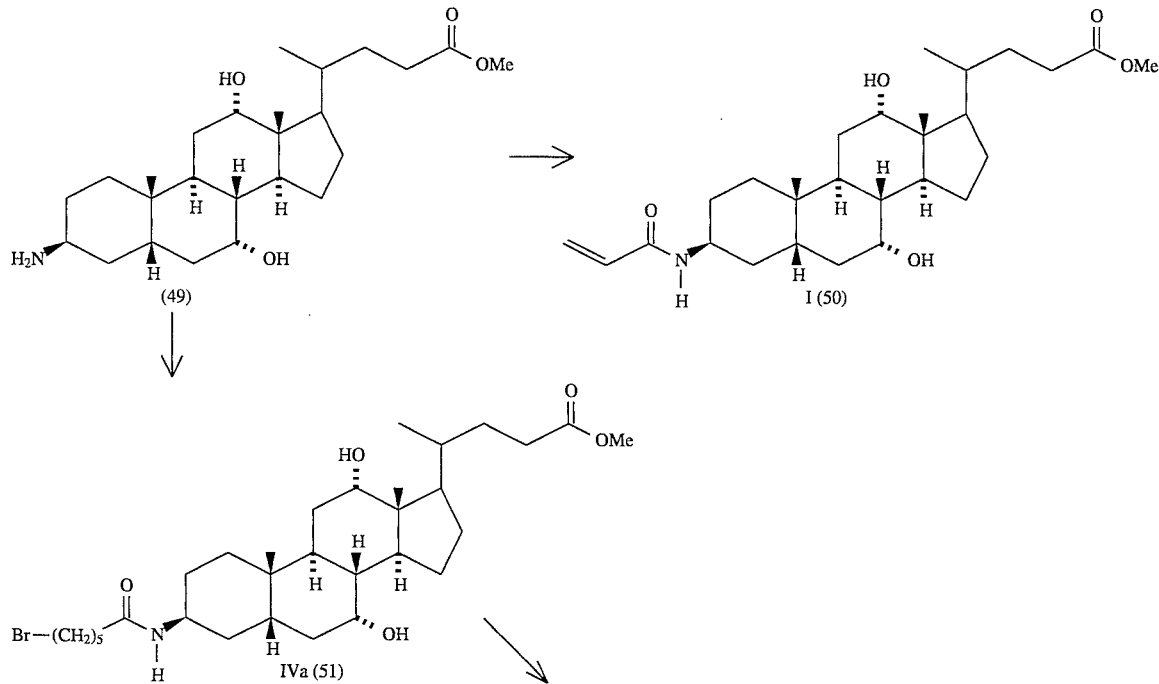

-continued
Reaction scheme 7

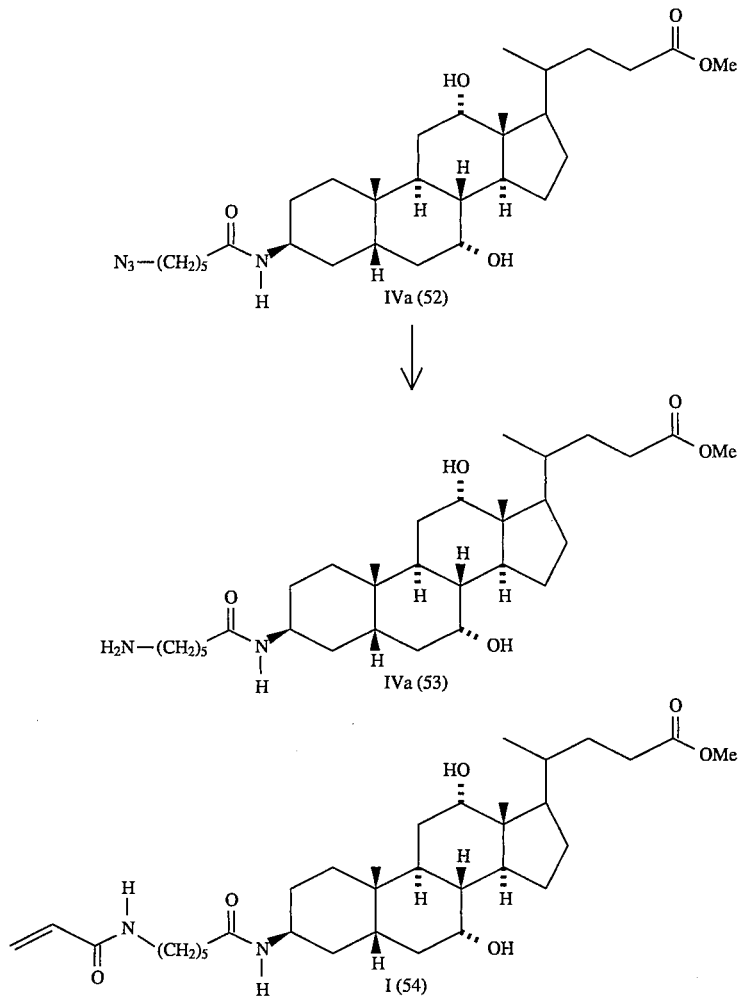

8) Compounds of the formula I, in which o=zero, Z=alkylene or aralkylene, A is

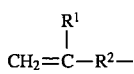

in which $R^2$ is a single bond and

is a free acid, its alkaline metal salt or an ester which can be hydrolyzed by base, can be prepared as follows:

The 3-keto bile acid derivative (55) is reacted with Grignard compounds derived from protected ω-hydroxyhaloalkanes. For example, trimethylsilyloxypropyl magnesium bromide is added to the compound (55) in ether or tetrahydrofuran at temperatures from 20° to 70° C. The diastereomer mixture IVa (56) results therefrom in a ratio of about 3:1, and can be separated by chromatography. The silyl protective group can be deprotected using tetrabutylammonium fluoride in tetrahydrofuran or alternatively ether at 0°–40° C. with the formation of the alcohol IVa (57).

X groups can also be introduced which already contain a polymerizable double bond. The ketone (55) can be reacted with ω-vinylalkylmagnesiumbromide or vinylalkylmagnesium iodide compounds which can be prepared therefrom. For example, under the conditions described above for Grignard reactions, a chromatographically separable diastereomer mixture of the vinyl compounds IVa (58) in a ratio of about 5:1 can be obtained from vinyl-magnesium bromide and the ketone (55). Under the same reaction conditions, the compounds IVa (59) are also obtained in a ratio of greater than 10:1 by reaction of butenylmagnesium iodide with the ketone (55).

These polymerizable compounds can also be reacted to give other important synthetic components. For example, the double bond of the compound IVa (59) can be converted into the hydroxy compound IVa (60), which in turn corresponds to a compound of the type IVa (57), by hydroboration with borane or 9-borabicyclononane in a solvent such as, for example, tetrahydrofuran, at −10°–40° C.

The reactions described are summarized in reaction scheme 8.

Reaction Scheme 8
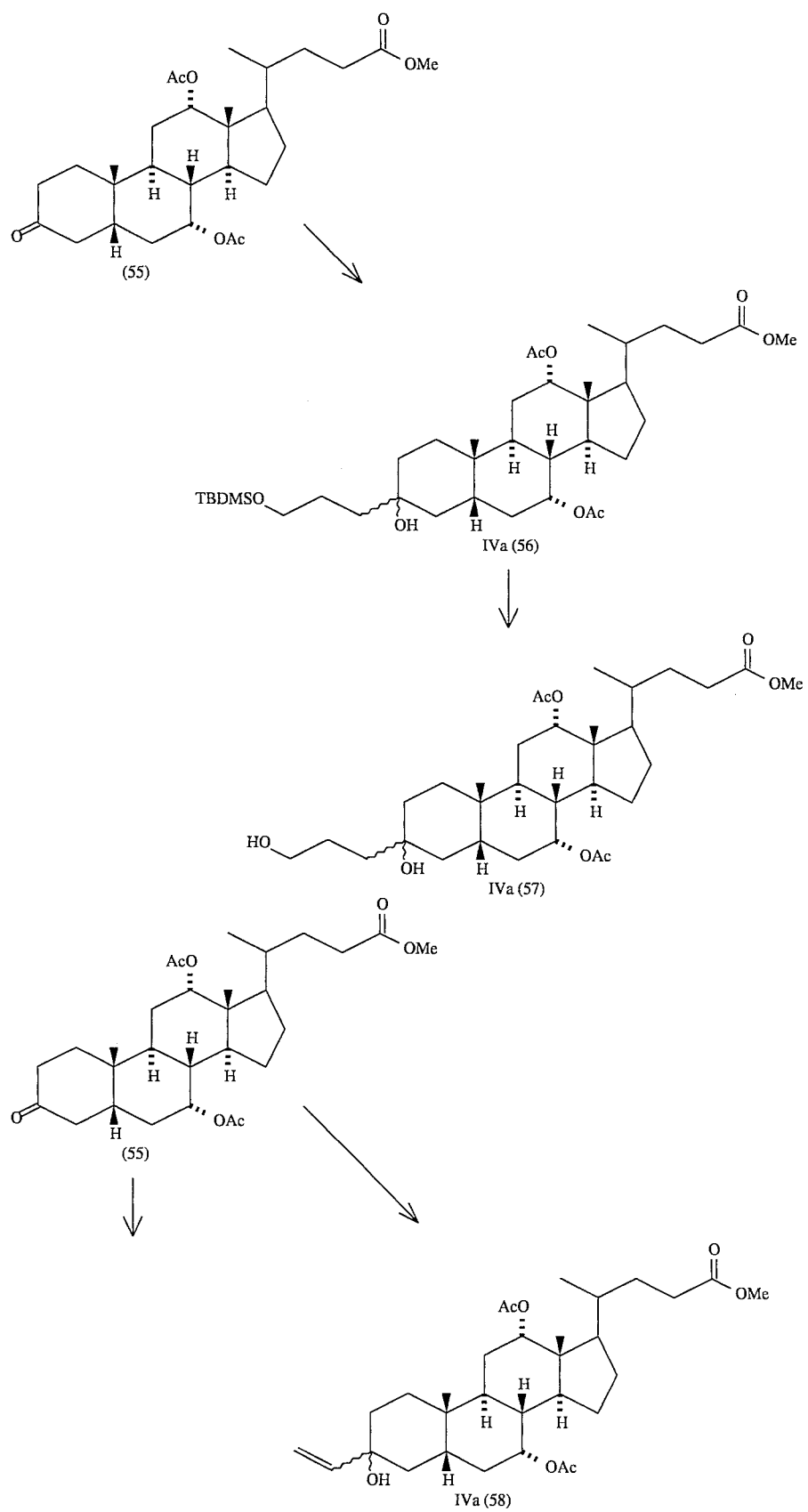

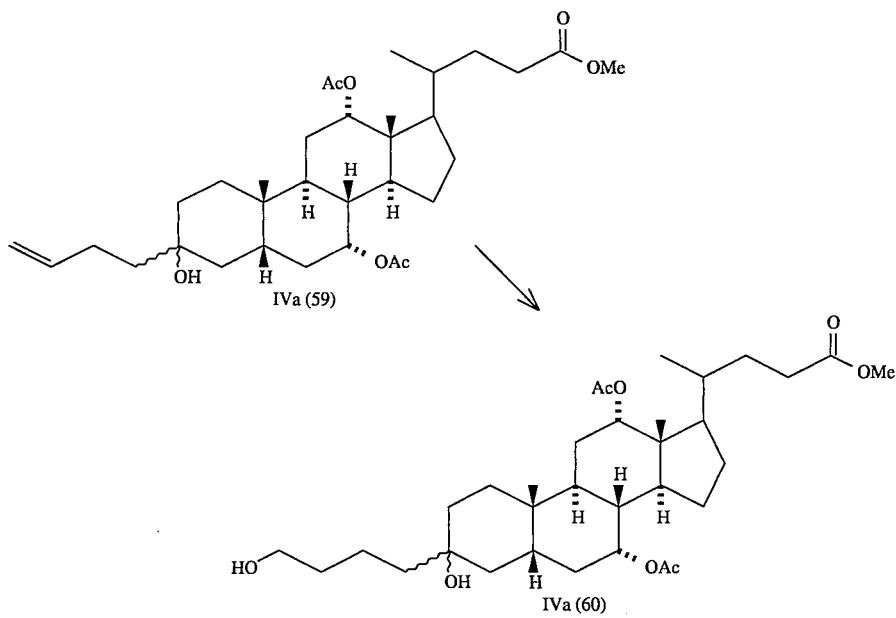

9) Compounds of the formula I in which Z is alkylene, where at least one methylene group is replaced by $$-NR'-\underset{\underset{O}{\|}}{C}-NR''-,$$

can also be reacted, like amino compounds of the type (8), with isocyanates which contain a polymerizable group to give the desired bile acid derivatives. If, for example, the isocyanate (61) is reacted with the amine (8) in a suitable solvent, such as, for example, dichloromethane, trichloromethane or tetrahydrofuran at temperatures from $-10°$ to $30°$ C., the compound I (62) is obtained. By basic hydrolysis of the methyl ester function with sodium hydroxide in ethanol/water, the free carboxylic acid I (63) is obtained.

By the same process, the compound I (65) in which the functional group is bonded via the 7-position of the bile acid is obtained by reaction of the amine (64) with the isocyanate (61).

The reaction described is summarized in reaction scheme 9

Reaction scheme 9

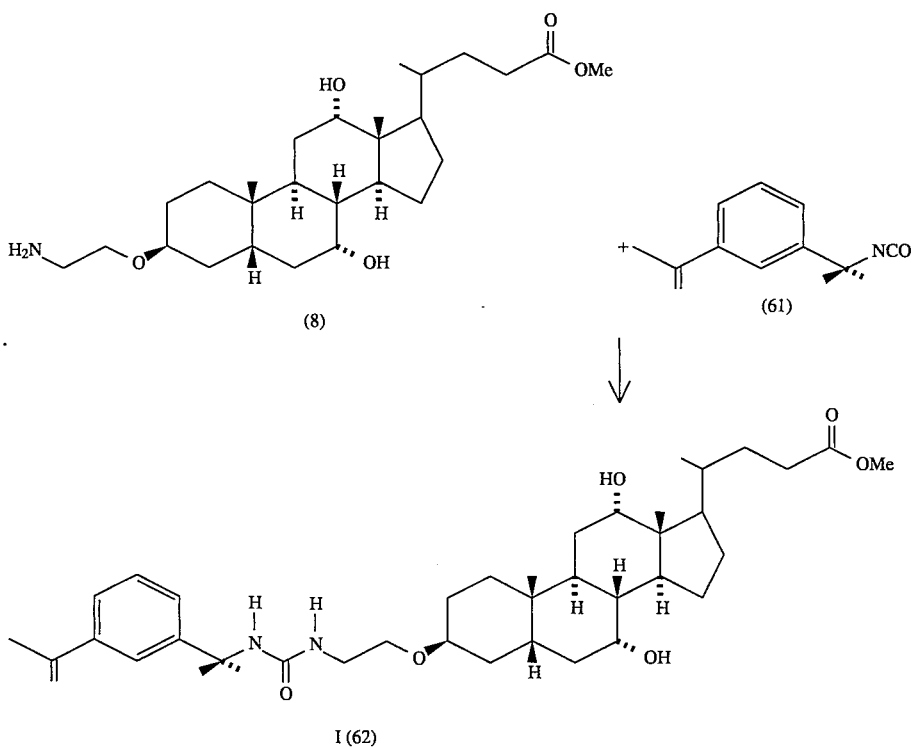

-continued
Reaction scheme 9

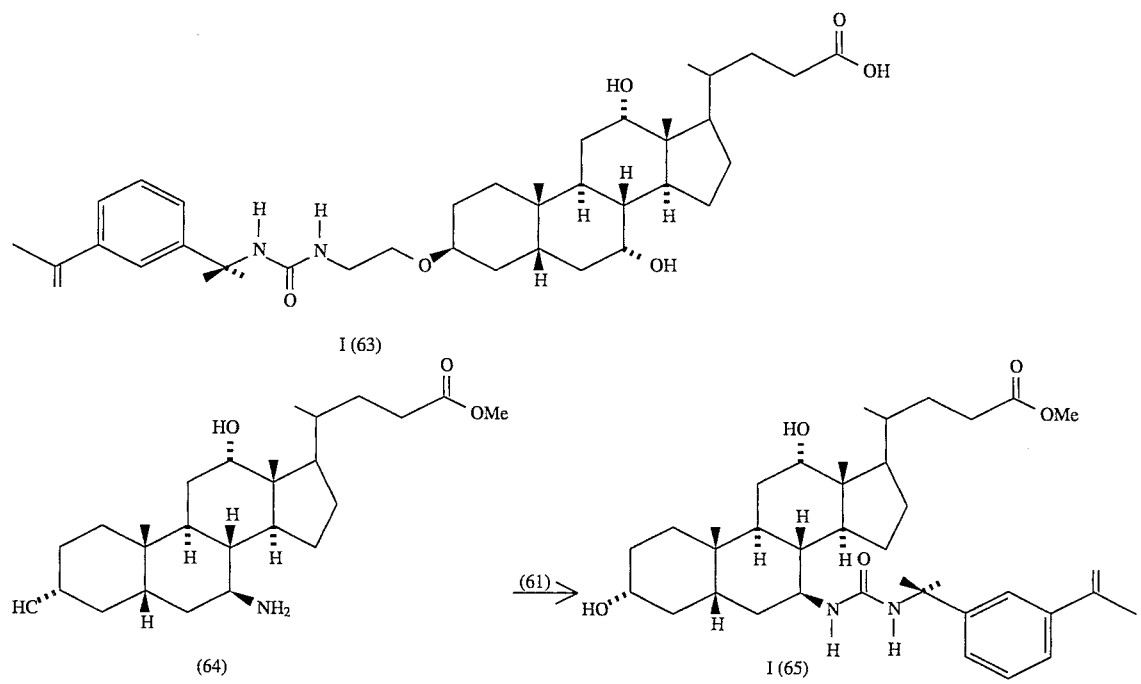

I (63)

(64)

I (65)

EXAMPLE 1

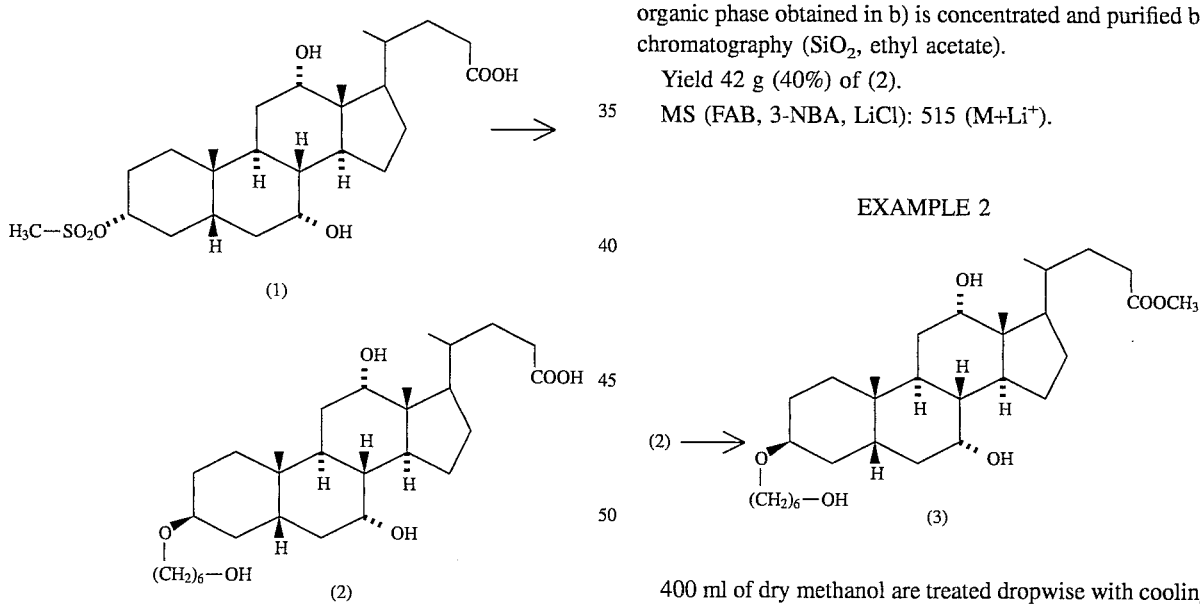

(1)

(2)

100 g (0.205 mol) of (1) are added to a mixture of 570 g of 1,6-hexanediol and 120 ml of pyridine and it is heated to 100° C. in the course of 45 min. The mixture is stirred at 100° C. for 3 h, cooled, treated with 120 ml of conc. $H_2SO_4$ in 2.5 l of water and stirred at room temperature for 1 h. It is extracted several times with ethyl acetate, and the organic phase is dried and concentrated. The residue is treated with water/ether in an extractor a) with the addition of 2 N NaOH until there is a distinct alkaline reaction and then b) after acidifying to pH 2–3 using half-concentrated HCl. The organic phase obtained in b) is concentrated and purified by chromatography ($SiO_2$, ethyl acetate).

Yield 42 g (40%) of (2).

MS (FAB, 3-NBA, LiCl): 515 (M+Li$^+$).

EXAMPLE 2

(3)

400 ml of dry methanol are treated dropwise with cooling with 40 ml of acetyl chloride. After 1 h at room temperature, 40 g (78.6 mmol) of (2), dissolved in 70 ml of methanol, are added, and the mixture is stirred at room temperature for 1 h and allowed to stand overnight in a refrigerator. It is poured into 2 l of ice-water, neutralized with satd. hydrogen carbonate solution and extracted several times using ether. The organic phase is dried and concentrated and the residue is purified by chromatography ($SiO_2$, ethyl acetate/heptane= 4:1). 31.5 g (77%) of (3) are obtained.

MS (FAB, 3-NBA, LiCl): 529 (M+Li$^+$).

EXAMPLE 3a

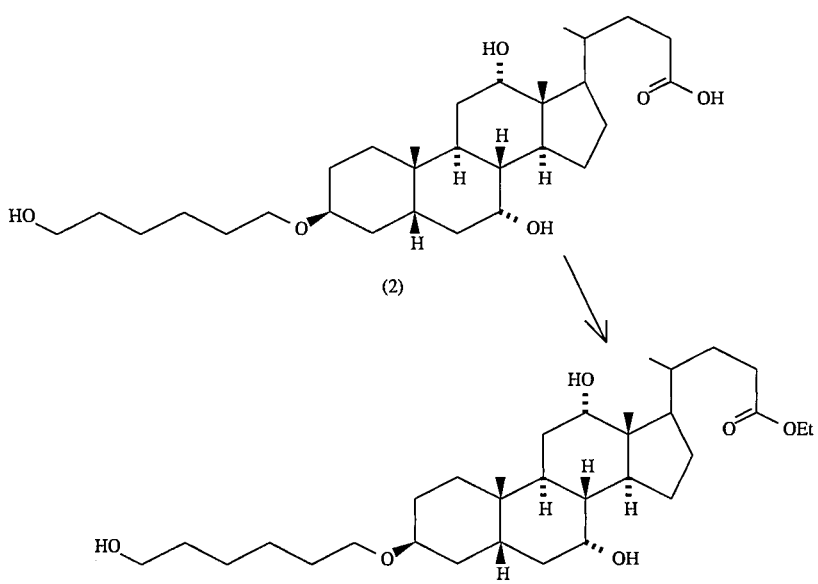

With ice-cooling, 2 ml of acetyl chloride are added dropwise to 20 ml of anhydrous ethanol. After 5 minutes, 2.0 g (3.93 mmol) of (2) are added. The reaction mixture is stirred overnight at room temperature. It is added to 50 ml of water and extracted 3 times using ether. The combined organic phases are washed with saturated $NaHCO_3$ solution, dried over $MgSO_4$ and concentrated. Chromatography on silica gel (ethyl acetate, also ethyl acetate/methanol=9:1) gives 1.9 g (3.54 mmol, 90%) of ethyl ester.

$C_{32}H_{58}O_6$ (536), MS (FAB, 3-NBA, LiCl): 543 (M+Li$^+$).

$C_{33}H_{58}O_6$ (550), MS (FAB, 3-NBA, LiCl): 557 (M+Li$^+$).

EXAMPLE 3b

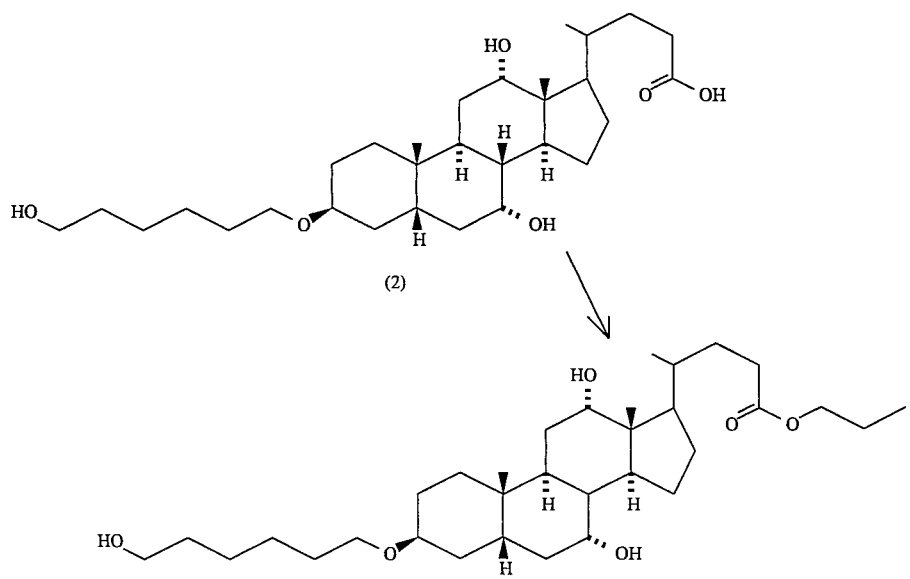

Starting from 2.0 g (3.93 mmol) of (2), 20 ml of n-propanol and 2 ml of acetyl chloride, 1.8 g (3.27 mmol, 83%) of n-propyl ester are prepared by the process described for Example 3a.

EXAMPLE 3c
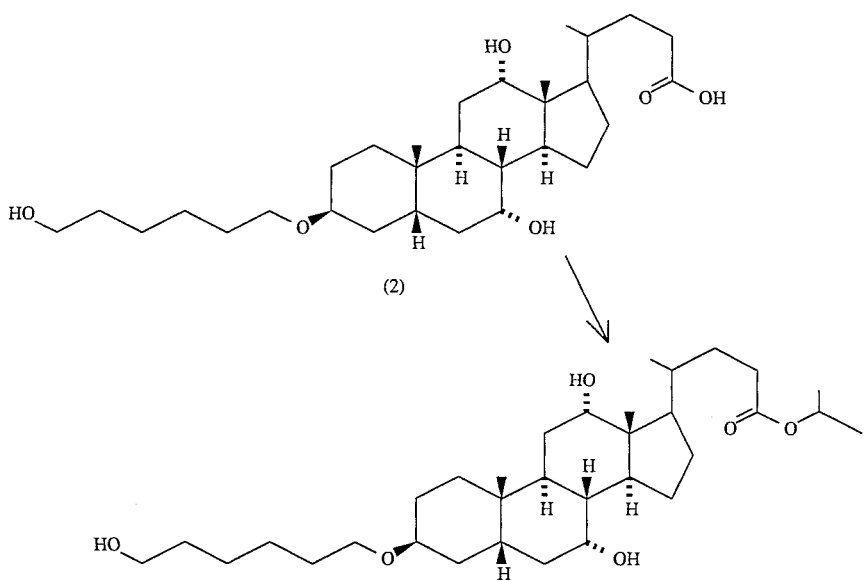
Starting from 2.0 g (3.93 mmol) of (2), 30 ml of i-propanol and 2 ml of acetyl chloride, 1.73 g (3.14 mmol, 80%) of i-propyl ester are prepared by the process described for Example 3a.
$C_{33}H_{58}O_6$ (550), MS (FAB, 3-NBA, LiCl): 557 (M+Li$^+$).
EXAMPLE 3d
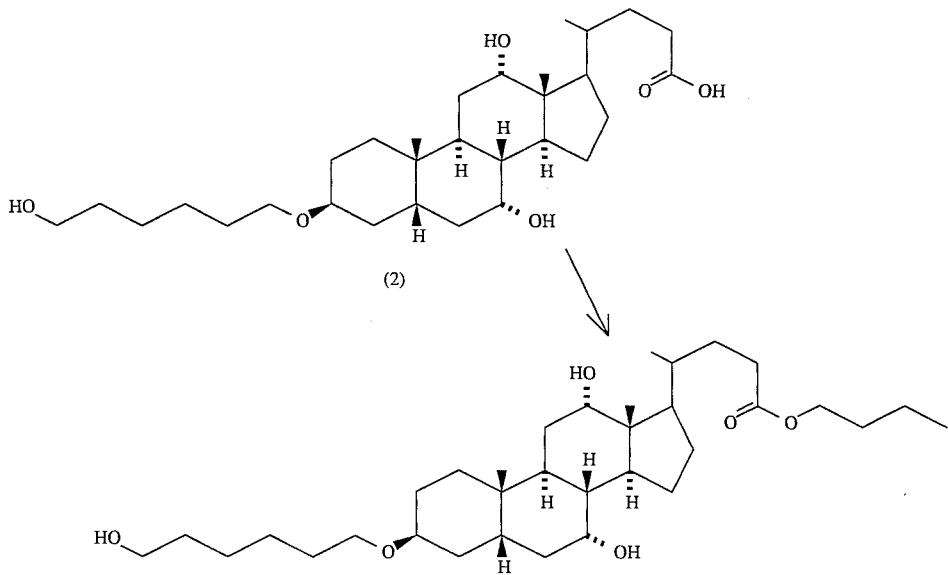
Starting from 2.0 g (3.93 mmol) of (2), 30 ml of n-butanol and 3 ml of acetyl chloride, 2.1 g (3.72 mmol, 95% of n-butyl ester are prepared by the process described for Example 3a.
$C_{34}H_{60}O_6$ (564), MS (FAB,3-NBA, LiCl): 571 (M+Li$^+$).

EXAMPLE 4

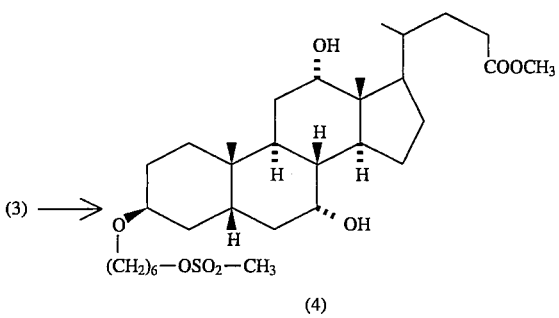

30 g (57.4 mmol) of (3) are cooled to 0° C. in 150 ml of dry pyridine and treated in portions in the course of 2–3 h with 8.3 ml of methanesulfonyl chloride with checking by thin layer chromatography. After reaction is complete, the mixture is added with ice-cooling to 120 ml of conc. $H_2SO_4$ in 1.5 l of water and shaken several times with ethyl acetate. The organic phase is dried and concentrated and the residue is purified by chromatography ($SiO_2$, ethyl acetate). Yield: 31.4 g (91%) of (4). MS (FAB, 3-NBA, LiCl): 607 (M+LI$^+$).

EXAMPLE 5

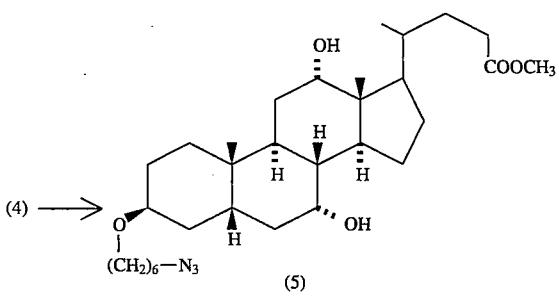

32.6 g (54.2 mmol) of (4) are treated under argon with 4.6 g of sodium azide in 800 ml of dimethylformamide and the mixture is heated at 80° C. for 2 h. It is allowed to stand overnight at room temperature, poured into 1 l of water and extracted several times with ethyl acetate. The organic phase is dried and concentrated. The residue is treated with water and extracted several times with ether. After drying and removal of the solvent, 26 g of (5) are obtained, which can be further employed as the crude product. MS (FAB, 3-NBA, LiCl): 554 (M+Li$^+$).

EXAMPLE 6a

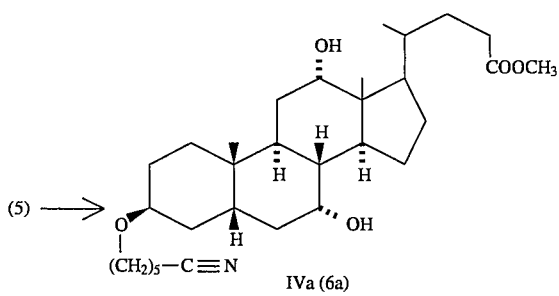

25.9 g of crude product (5) are dissolved in 500 ml of ethyl acetate and hydrogenated with 5 g of palladium/carbon (10%) in a shaking duck. After reaction is complete, the solid is filtered off with suction, the filtrate is concentrated and the residue is purified by column chromatography ($SiO_2$, ethyl acetate). 17.1 g of IVa (6a) are obtained (61% based on (4)).

MS (FAB, 3-NBA, LiCl): 524 (M+Li$^+$).

EXAMPLE 6b

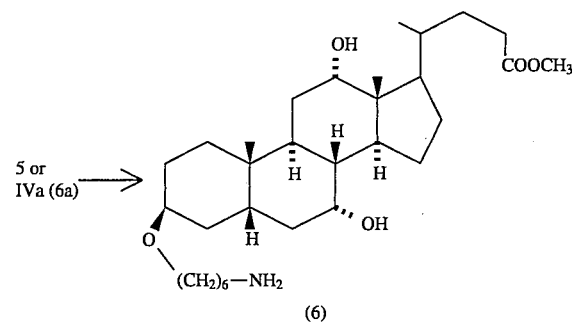

17 g (32.8 mmol) of IVa (6a) are dissolved in 500 ml of methanol+about 50 ml of conc. ammonia water, and the solution is treated with 4 g of 5% strength rhodium on $Al_2O_3$ and hydrogenated at 20 bar of $H_2$ at room temperature. After reaction is complete, the solid is filtered off with suction, the filtrate is concentrated and the residue is purified by chromatography ($SIO_2$, $CH_2Cl_2$/MeOH/$NH_3$ conc.=100:10:5). 12.7 g (74%) of (6) are obtained.

MS (FAB, 3-NBA, LiCl): 528 (M+LI$^+$), 522 (M+H$^+$).

(6) can also be prepared directly from the crude product (5) by hydrogenation over rhodium on $Al_2O_3$ under the above mentioned conditions. Starting from 20 g of crude product (5), 9.6 g of (6) are obtained (42% based on (4)).

EXAMPLE 7

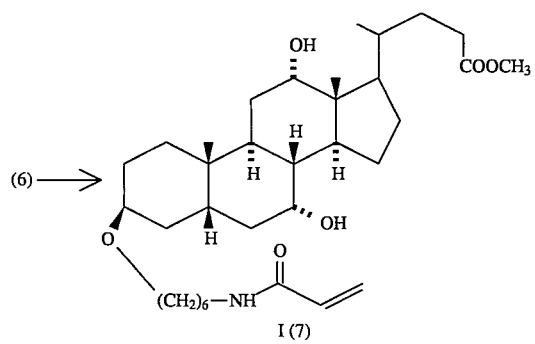

4.5 g (8.6 mmol) of (6) and 1.4 ml of triethylamine are treated dropwise with 1 ml of acryloyl chloride in 10 ml of $CH_2Cl_2$ in 200 ml of dry $CH_2Cl_2$ at −8° C. to −4° C.

After 1 h at 0° C. and 1 h at room temperature, the mixture is poured into water and extracted with $CH_2Cl_2$, and the organic phase is washed, dried and concentrated. After chromatography ($SiO_2$, ethyl acetate), 3.5 g (70.5%) of I (7) are obtained.

Melting point: 125° C. MS (FAB, 3-NBA, LiCl): 562 (M+Li$^+$).

EXAMPLE 8

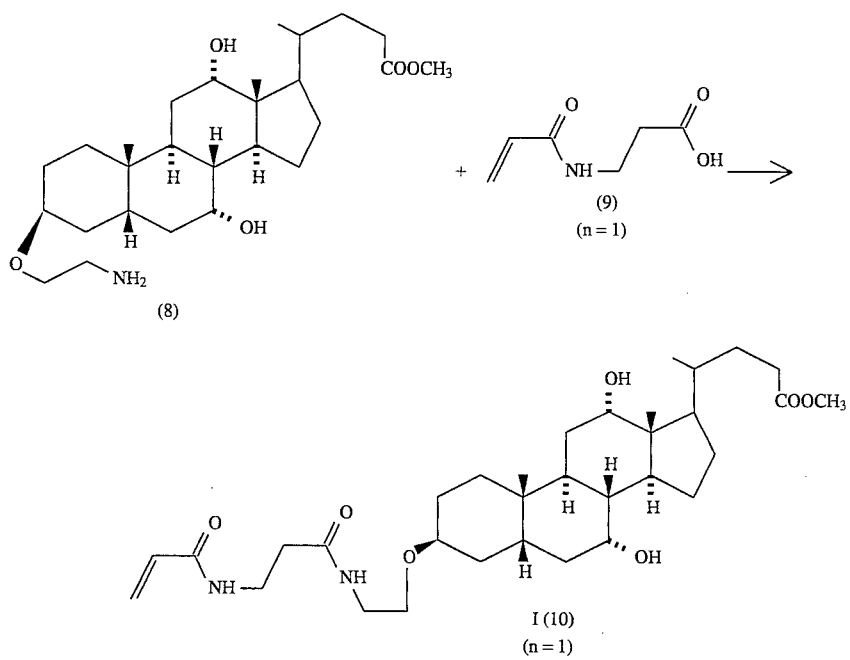

1.91 g (4.1 mmol) of (8) are dissolved in 200 ml of purified ethyl acetate with 0.61 ml of triethylamine and 30 mg of hydroquinone. 1.1 g of ethyl 1,2 dihydro-2-ethoxyquinoline-1-carboxylate (EEDQ) and 572 mg of (9) are added to this solution and it is heated to reflux for several hours with checking by thin layer chromatography.

After reaction is complete, the mixture is diluted with 200 ml of ethyl acetate, and washed with $KHSO_4$ solution and with water. The organic phase is dried and concentrated. Chromatography of the residue ($SiO_2$, ethyl acetate/MeOH= 10:1) gives 1.2 g (50%) of 1 (10).

MS (FAB, 3-NBA, LiCl): 597 (M+Li$^+$).

EXAMPLE 9

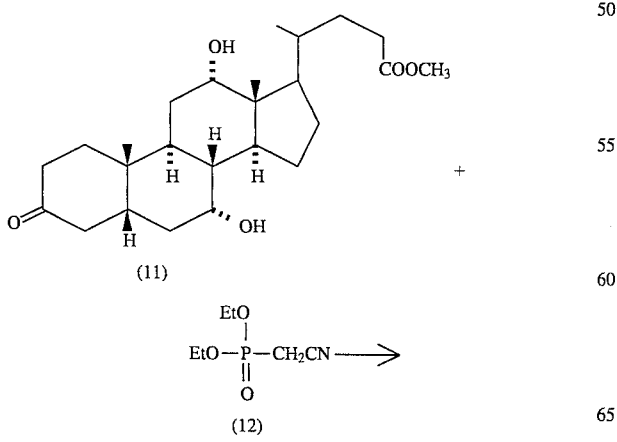

-continued

[structure IVa (13)]

4.4 g of 60% sodium hydride suspension are introduced into 250 ml of drymethanol with cooling and under argon. 18 ml (0.11 mol) of diethyl cyanomethylphosphonate (12) are added dropwise to this mixture and it is stirred at room temperature for 1 h. 42 g (0.1 mol) of (11) in 450 ml of methanol are then added dropwise and the mixture is stirred at room temperature for 2 h. The reaction mixture is concentrated in the cold and the residue is partitioned between $CH_2Cl_2$ and water. The separated aqueous phase is extracted several times using $CH_2C_2$. The organic phases are dried and concentrated and the residue which remains is purified by chromatography ($SiO_2$, ethyl acetate/cyclohexane=1:1). 34.5 g (78%) of IVa (13) are obtained.

MS (FAB, 3-NBA, LiCl): 450 (M+Li$^+$).

EXAMPLE 10

IVa (13) ⟶

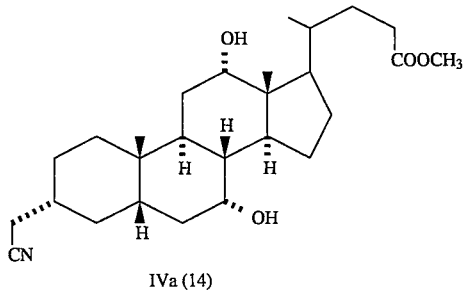

IVa (14)

35 g (78.8 mol) of IVa (13) are dissolved in 1.2 l of methanol and hydrogenated in a shaking duck with 5 g of 10% palladium/carbon. After filtration, concentration and chromatography (SiO$_2$, ethyl acetate, cyclohexane=4:1), 33.5 g (95%) of IVa (14) are obtained.

MS (FAB, 3-NBA, LiCl): 452 (M+Li$^+$).

In this product, the 3α-isomer predominates according to analysis of IVa (15) [prepared according to a) and b)] in the ratio≧95:5.

EXAMPLE 11

IVa (14) ⟶ a) 15 g (33.8 mmol) of IVa (14) are hydrogenated with 4 g of 5% rhodium on Al$_2$O$_3$ for 24 hours at room temperature and 20–25 bar of H$_2$ in 800 ml of methanol and 10 ml of conc. aqueous ammonia. After filtration, concentration and chromatography of the residue, 12.5 g (81%) of IVa (15) are obtained as the about 1:1 3α/3β-isomer mixture.

The stereoisomers are separated by column chromatography (SiO$_2$, CH$_2$Cl$_2$/MeOH/conc. aq. NH$_3$=100:15:5).

b) 33 g (74 mmol) of IVa (14) are hydrogenated for 24 hours with 8 g of 5% rhodium on Al$_2$O$_3$ at 20 bar of hydrogen at room temperature in 1.6 ml of methanol and 20 ml of conc. aq. ammonia. After filtration, concentration and chromatography (SiO$_2$/CH$_2$Cl$_2$/MeOH/conc. aq. NH$_3$= 100:15:5), 0.9 g (2.7%) of less polar 3β-IVa (15) and 28.8 g (86.5%) of polar 3α-isomer IVa (15) are obtained [3α/3β= 97:3].

EXAMPLE 12

IVa (15) ⟶

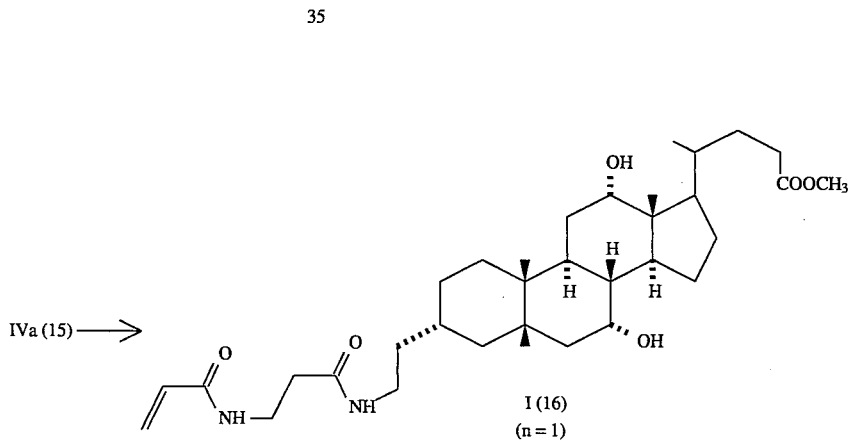

I (16)
(n = 1)

-continued

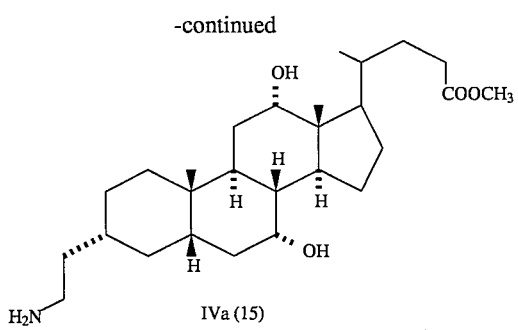

IVa (15)

1.4 g (3.1 mmol of IVa (15) are heated to reflux for 4 h with 0.45 ml of triethylamine, 20 g of hydroquinone and 850 mg of EEDQ in 150 ml of THF.

The major part of the solvent is removed in vacuo, and the mixture is diluted with ethyl acetate and washed with KHSO$_4$ solution and water. The organic phase is dried, concentrated and purified by chromatography (SiO$_2$, ethyl acetate/MeOH=10:1). 1.2 g (67%) of I (16) are obtained.

MS (FAB, 3-NBA, LiCl): 581 (M+Li$^+$).

EXAMPLE 13

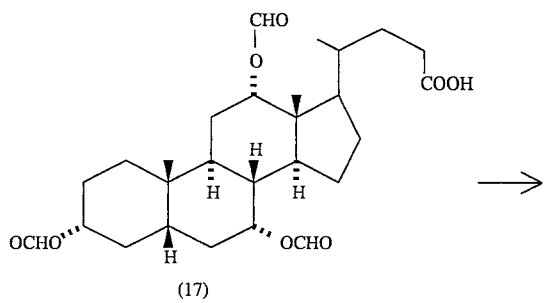
(17)

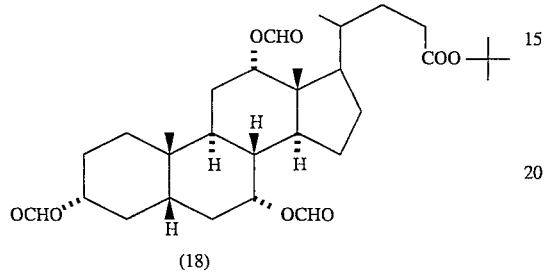
(18)

40 ml of thionyl chloride freshly distilled over quinoline and linseed oil are added to 20 g (40.5 mmol) of (17) in 400 ml of dry toluene and the mixture is heated at 80° C. for 4 hours under argon. The excess $SOCl_2$ is removed to the greatest possible extent by distilling several times with toluene, the residue is taken up using 100 ml of dry $CH_2Cl_2$ and the solution is added at 0° C. to a mixture of 100 ml of tert-butanol, 100 ml of $CH_2Cl_2$ and 4 ml of pyridine. It is stirred at room temperature for 2 hours, and then poured into water and extracted using $CH_2Cl_2$ after separating off the organic phase, and the residue which remains is purified by chromatography after drying and concentration ($SiO_2$; $CH_2Cl_2$/acetate=4:1).

18.1 g (81%) of (18) are obtained.

MS (FAB, 3-NBA, LiCl): 555 (M+Li$^+$).

EXAMPLE 14

(18) ⟶

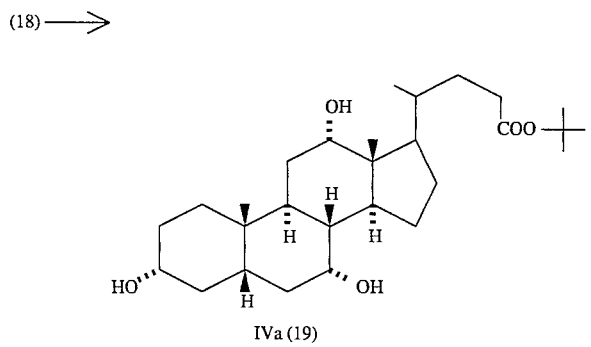
IVa (19)

18 g (32.8 mmol) of (18) are heated on a steam bath for 10 min in 250 ml of dioxane and 100 ml of 2N NaOH. The mixture is then concentrated in vacuo to about one half and treated with 400 ml of $CH_2Cl_2$ and water until the phases separate. After separation of the organic phase, extraction with $CH_2Cl_2$, drying and concentration, the residue is purified by column filtration. 14.8 g (97%) of IVa (19) are obtained.

MS (FAB, 3-NBA, LiCl): 471 (M+Li$^+$).

EXAMPLE 15

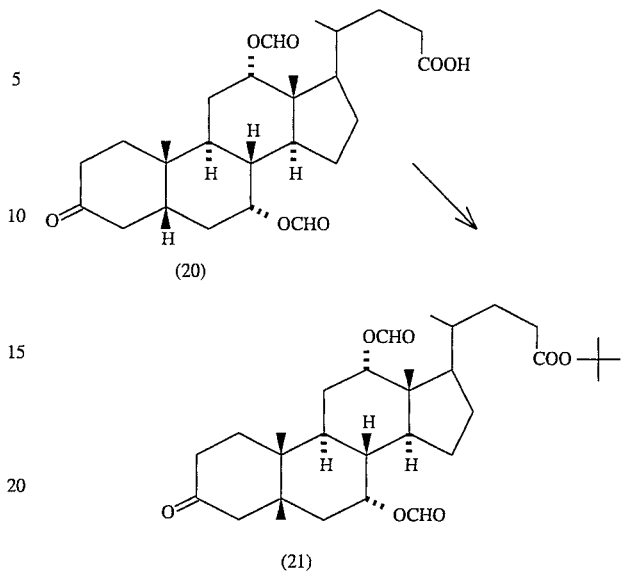
(20)

(21)

2 g (4.3 mmol) of (20) in 20 ml of dry toluene are treated with 4 ml of oxalyl chloride and the mixture is stirred at 80° C. for 4 hours. The excess oxalyl chloride is then removed by distillation with toluene (addition twice) and the residue is taken up in 20 ml of dry $CH_2Cl_2$. The solution is added at 0° C. to a mixture of 10 ml of $CH_2Cl_2$, 10 ml of tert-butanol and 0.4 ml of pyridine. After 2 hours at room temperature, it is treated with water, the organic layer is separated off, extracted, dried and concentrated and the residue is purified by chromatography ($SiO_2$, $CH_2Cl_2$/acetone=10:1).

Yield: 1.43 g (64%) of I (21).

MS (FAB, 3-NBA, LiCl): 525 (M+Li$^+$).

EXAMPLE 16

(21) ⟶ 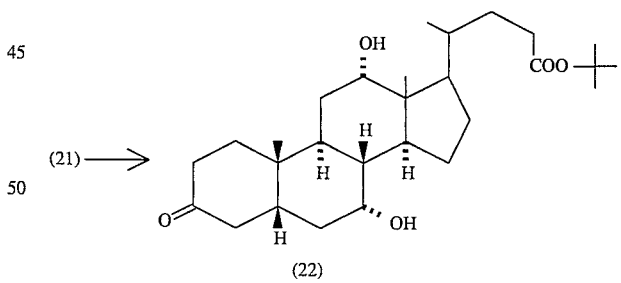
(22)

15 g (32.3 mmol of I (21) and 20 g of aluminum tert-butoxide are heated to reflux for 28 hours under argon in a mixture of 450 ml of dry toluene and 190 ml of dry acetone. After cooling, the mixture is poured with cooling onto 300 ml of 2N $H_2SO_4$ and extracted three times with ether. The organic phase is washed twice with 2N $H_2SO_4$, twice with water, twice with satd. $NaHCO_3$ solution and again with water, and is dried and concentrated. Column chromatography ($SiO_2$, $CH_2Cl_2$/acetone=4:1) gives 9.7 g (65%) of (22).

MS (FAB, 3-NBA, LiCl): 469 (M+Li$^+$).

EXAMPLE 17

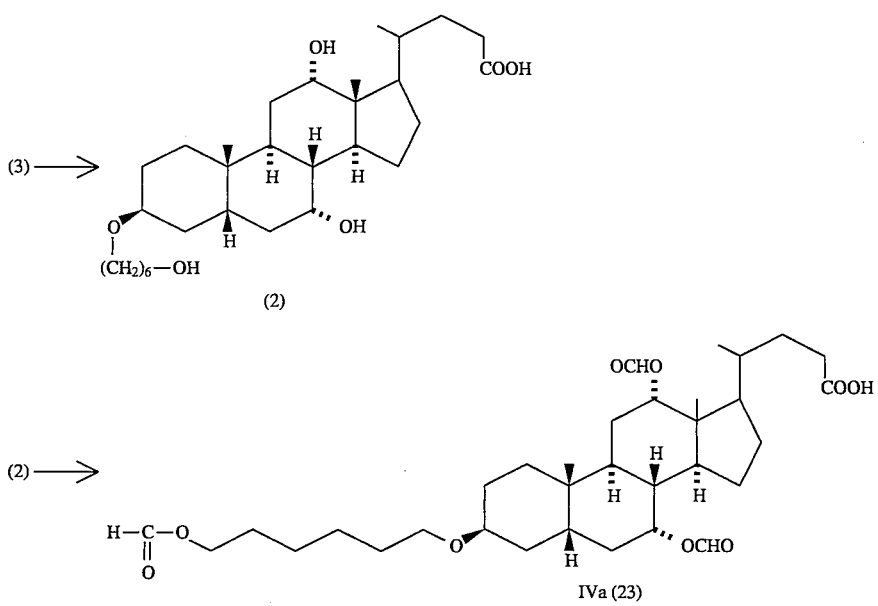

Starting from (3), compound (2) is prepared by the process described in Example 26.

5.1 g (0.01 mol) of (2) are heated at 55°–60° C. for 1.5 hours in 25 ml of 90 percent formic acid and 8 drops of 60 percent perchloric acid. After cooling to 40° C., 15 ml of acetic anhydride are added dropwise until a distinct evolution of gas occurs (temperature increase 40° to 50° C.). The solution is cooled to room temperature and poured with vigorous stirring in 200 ml of water, and the product is extracted using dichloromethane.

After drying and evaporation, and recrystallization of the residue from $CH_3OH/H_2O$, 5.44 g (92%) of IVa (23) are obtained.

MS (FAB, 3-NBA, LiCl): 599 (M+Li$^+$).

EXAMPLE 18

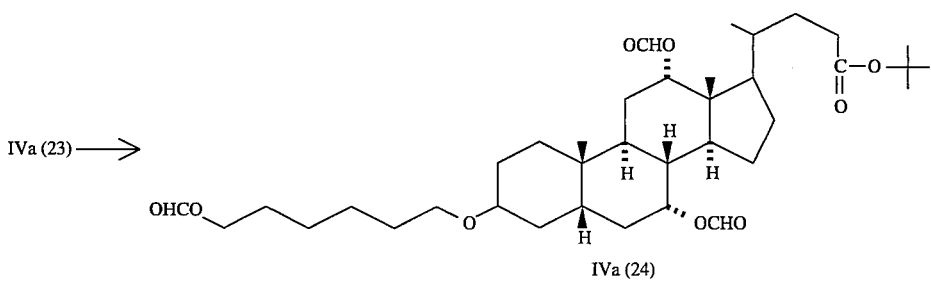

8 ml of thionyl chloride freshly distilled over quinoline and linseed oil are added to 4 g (6.75 mmol) of IVa (23) in 80 ml of dry toluene and the mixture is heated to 80° C. for 4 hours under argon. The excess $SOCl_2$ is then distilled off with toluene and removed to the greatest possible extent by twice adding toluene and distilling again. The residue is taken up using 50 ml of dry $CH_2Cl_2$ and the solution is added at 0° C. to a solution of 20 ml of tert-butanol in 40 ml of $CH_2Cl_2$ and 0.8 ml of pyridine. After storing at room temperature for 1 hour and standing overnight, the mixture is treated with water and, after separating off, the organic phase is extracted several times using $CH_2Cl_2$, dried and concentrated. The crude product is purified by chromatography ($SiO_2$, n-heptane/ethyl acetate=3:1).

Yield: 3.8 g (87%) of IVa (24).

MS (FAB, 3-NBA, LiCl): 655 (M+Li$^+$).

EXAMPLE 19

IVa (24) ⟶ 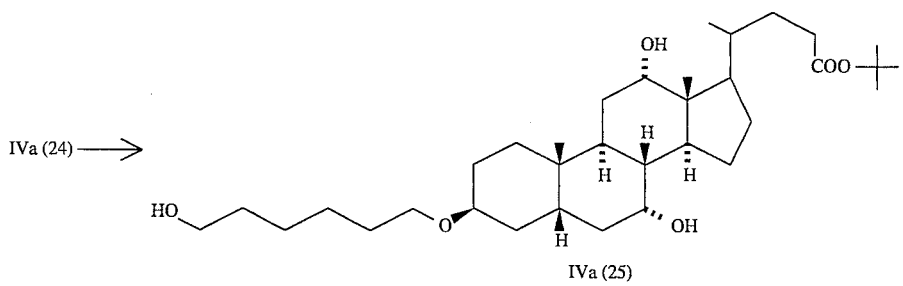

3.5 g (5.4 mmol) of IVa (24) are dissolved in 50 ml of dioxane and 20 ml of 2N NaOH and the mixture is heated on a steam bath for 10 min. It is diluted with 100 ml of $CH_2Cl_2$, roughly dried using $MgSO_4$, filtered and concentrated, and the residue is purified by column filtration.

3.05 g (93%) of IVa (25) are obtained.

MS (FAB, 3.-NBA, LiCl): 571 (M+Li$^+$).

reaction mixture is concentrated in vacuo. After chromatography of the residue on silica gel (ethyl acetate/methanol/triethylamine 5:1:1), 1.8 g (3.66 mmol, 57%) of allyl ester IVa (26) are obtained. $C_{29}H_{49}NO_5$ (491), MS (FAB, 3-NBA, LiCl): 498 (M+Li$^+$).

EXAMPLE 20

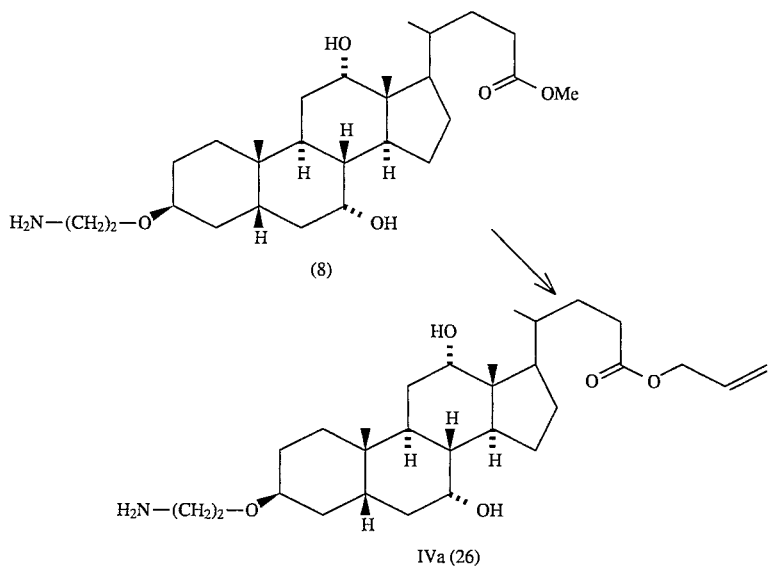

3.0 g (6.44 mmol) of methyl ester (8) (EP-A-0,417,725) and 0.43 g (1.88 mmol) of tetraethoxytitanium are stirred at 100° C. for 20 hours in 50 ml of dry allyl alcohol. The

EXAMPLE 21

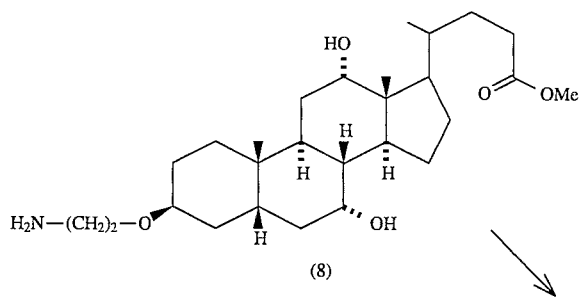

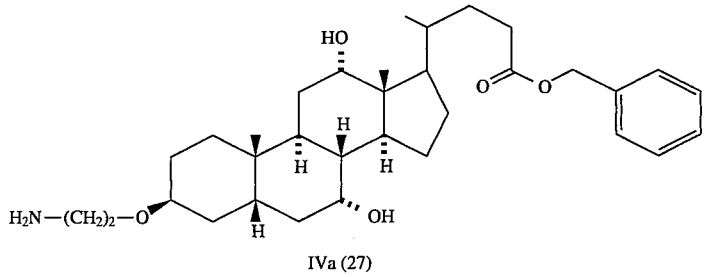

IVa (27)

15.0 g (32,21 mmol) of methyl ester (8) and 2,28 g (10 mmol) of tetraethoxytitanium are stirred at 100° C. for 8 hours in 300 ml of dry benzyl alcohol. The reaction mixture is concentrated in vacuo. After chromatography of the residue on silica gel (ethyl acetate/methanol/triethylamine 5:1:1), 10.0 g (18.46 mmol, 57%) of benzyl ester IVa (27) are obtained.

$C_{33}H_{51}NO_5$ (541), MS (FAB, 3-NBA, LiCl): 548 (M+Li$^+$).

EXAMPLE 22

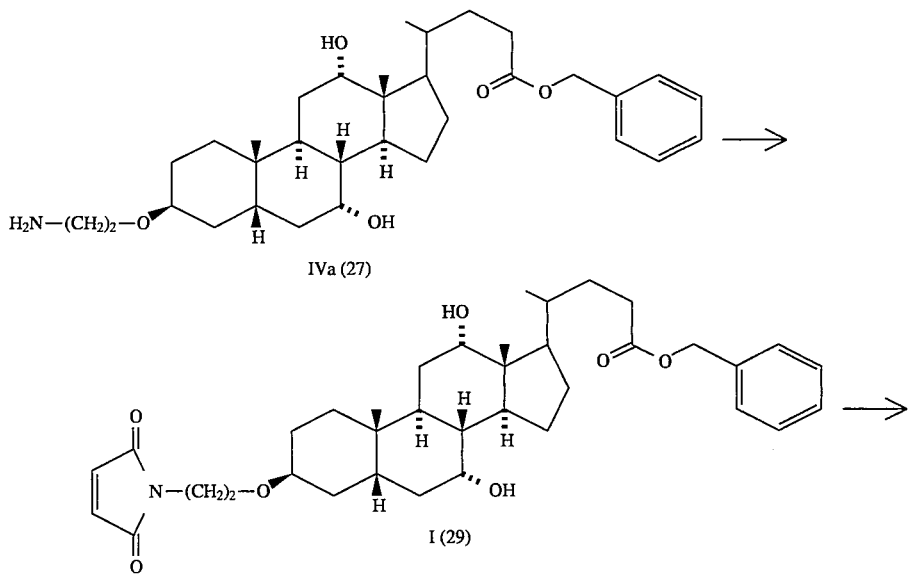

540 mg (1.00 mmol) of IVa (27) and 147 mg (1.50 mmol) of maleic anhydride are dissolved in 10 ml of acetic acid and heated under reflux for 4 hours. After cooling to room temperature, the solvent is stripped off in vacuo. Chromatography of the crude product on silica gel (ethyl acetate/methanol/triethylamine 15:4:1) gives 490 mg (0.79 mmol, 79%) of I (29).

$C_{37}H_{51}NO_7$(621), MS (FAB, 3-NBA, LiCl): 628 (M+Li$^+$).

EXAMPLE 23

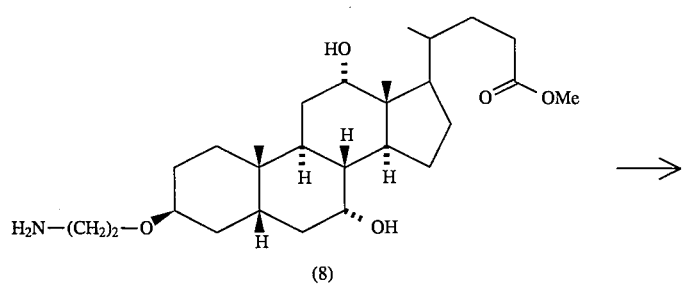

(8)

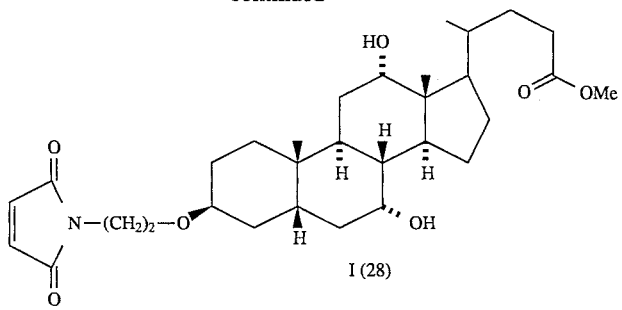

I (28)

460 mg (1.00 mmol) of (8) and 100 mg (1.00 mmol) of maleic anhydride are dissolved in 10 ml of acetic acid and heated under reflux for 4 hours. After cooling to room temperature, the solvent is stripped off in vacuo. Chromatography on silica gel gives 330 mg (0.60 mmol, 61%) of I (28).

$C_{31}H_{47}NO_7$ (545), MS (FAB, 3-NBA, LiCl): 552 (M+Li$^+$).

of triethylamine in 80 ml of tetrahydrofuran. After 30 min. at −30° C., the mixture is poured into water and extracted 3 times using ethyl acetate. The combined organic phases are dried over sodium sulfate and concentrated in vacuo. The residue is chromatographed on silica gel (ethyl acetate) and 3.2 g (6.16 mmol, 57%) of I (30) are obtained.

$C_{30}H_{49}NO_6$ (519), MS (FAB, 3-NBA, LiCl): 526 (M+Li$^+$).

EXAMPLE 24

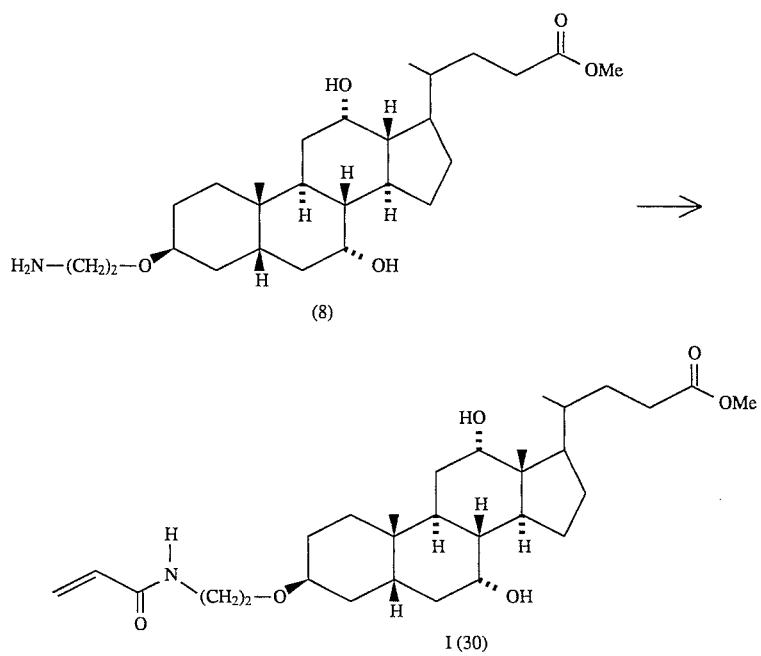

A solution of 0.94 ml (11.57 mmol) of acryloyl chloride in 20 ml of THF is slowly added dropwise at −30° C. to a solution of 5.0 g (10.74 mmol) of (8) and 1.8 ml (12.9 mmol)

EXAMPLE 25

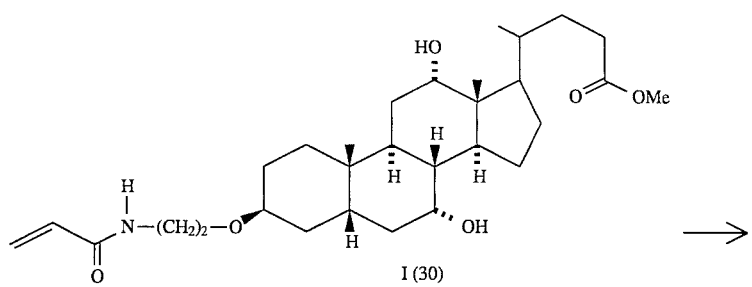

I (30)

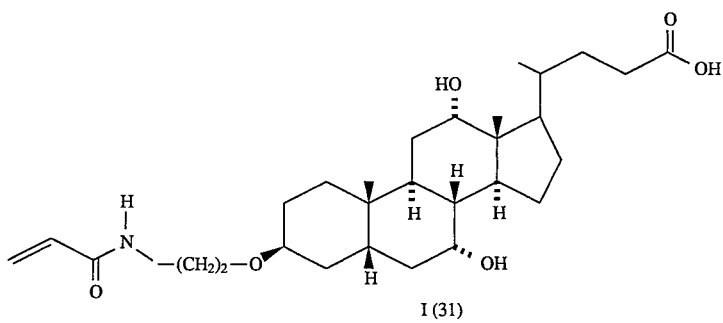

I (31)

500 mg (0.96 mmol) of I (30) are dissolved in 50 ml of ethanol, treated with 5 ml of 1N NaOH and stirred at room temperature for 3 hours. 50 ml of water are added, the alcohol is evaporated in vacuo, the residue is acidified with HCl and the mixture is extracted 3 times with ethyl acetate. The combined organic phases are dried over sodium sulfate and evaporated. Chromatography on silica gel (chloroform/methanol 9:1) gives 280 mg (0.55 mmol, 58%) of I (31).

$C_{29}H_{47}NO_6$ (505), MS (FAB, 3-NBA, LiCl): 512 (M+Li$^+$).

EXAMPLE 26

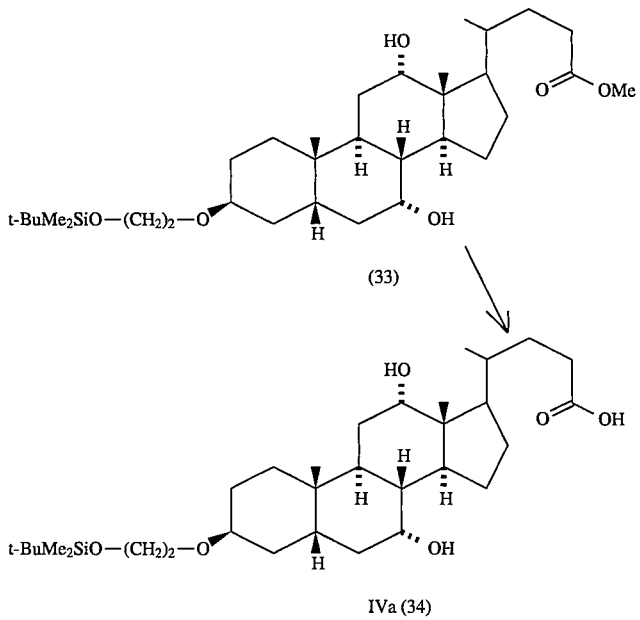

(33)

IVa (34)

21.2 g (36.5 mmol) of (33) (EP-A 0,417,725) are dissolved in methanol (500 ml) and heated under reflux. 43.7 ml of 1N NaOH are added dropwise in the course of 24 hours and the mixture is then heated under reflux for a further 6 hours. The solvent is then mainly stripped off, the residue is taken up in 400 ml of water, and the mixture is treated with 44.0 ml of 1N HCl and extracted 3 times with ether. The combined organic phases are dried (MgSO$_4$) and concentrated. Chromatography on silica gel gives 19.9 g (28 mmol, 77%) of IVa (34).

$C_{32}H_{58}O_6Si$ (566), MS (FAB, 3-NBA, LiCl): 573 (M+Li$^+$).

Melting point: 188°–190° C.

EXAMPLE 27

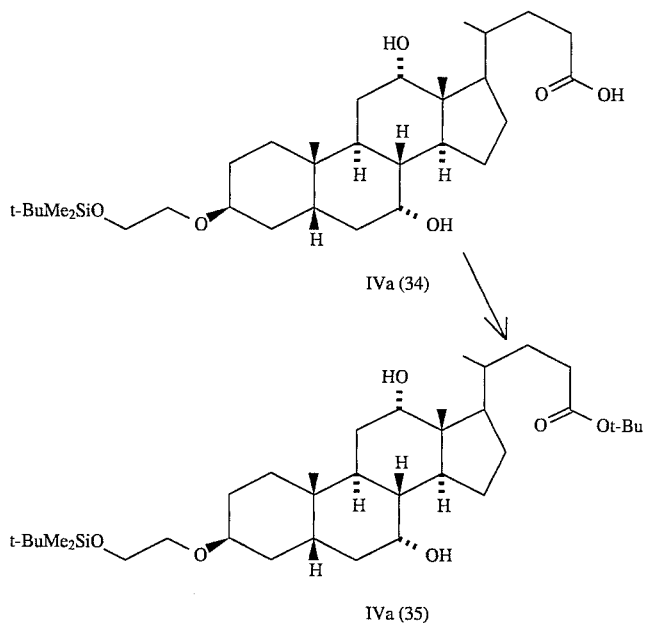

15.9 g (28.0 mmol) of IVa (34) and 3.68 g (36.5 mmol) of triethylamine are dissolved in 300 ml of tetrahydrofuran and cooled to 0° C. After addition of 7.03 g (33.6 mmol) of 2,6-dichlorobenzoyl chloride, the ice-bath is removed and the mixture is heated under reflux for 4 hours. 31.2 g (0.42 mol of t-butanol and 3.42 g (28 mmol) of dimethylaminopyridine are then added at room temperature. The mixture is heated under reflux for a further 4 hours. The solvent is largely distilled off, the residue is taken up in 300 ml of ethyl acetate, and the solution is washed 3 times with water and dried over magnesium sulfate. After stripping off the solvent, the residue is chromatographed on silica gel (cyclohexane/ethyl acetate 7:3) and 8.9 g (14.3 mmol, 51%) of IVa (35) are obtained.

$C_{36}H_{66}O_6Si$ (622), MS (FAB, 3-NBA, LiCl): 629 (M+Li$^+$).

EXAMPLE 28

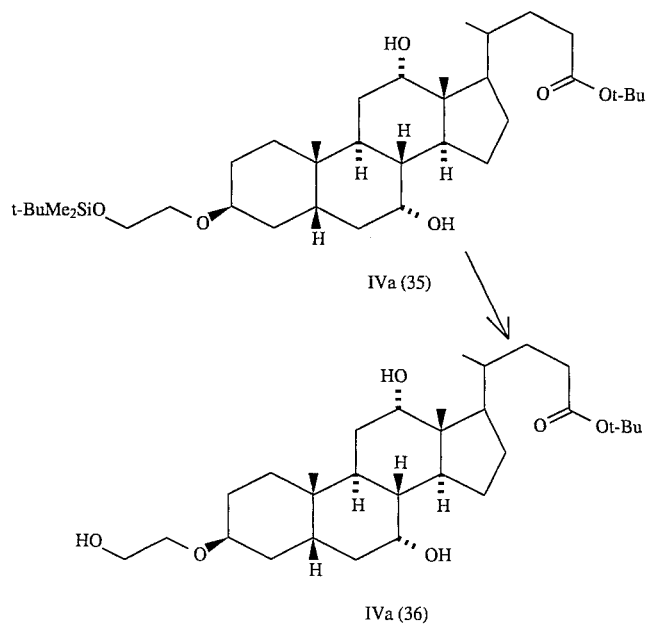

8.35 g (13.4 mmol) of compound IVa (33) are dissolved in 150 ml of tetrahydrofuran, treated with 3.21 g (53 mmol) of acetic acid and 12.94 g (40 mmol) of tetrabutylammonium fluoride trihydrate and stirred at room temperature for 20 hours. The solvent is distilled off, the residue is taken up in 200 ml of ethyl acetate, and the solution is washed 4 times with water and dried over magnesium sulfate. The crude product obtained after evaporation is chromatographed on silica gel (ethyl acetate/cyclohexane 9:1). 5.5 g (10.8 mmol, 81%) of IVa (36) are obtained.

$C_{30}H_{52}O_6$ (508), MS (FAB, 3-NBA, LiCl): 515 (M+Li$^+$).

Melting point 127°–129° C.

EXAMPLE 29

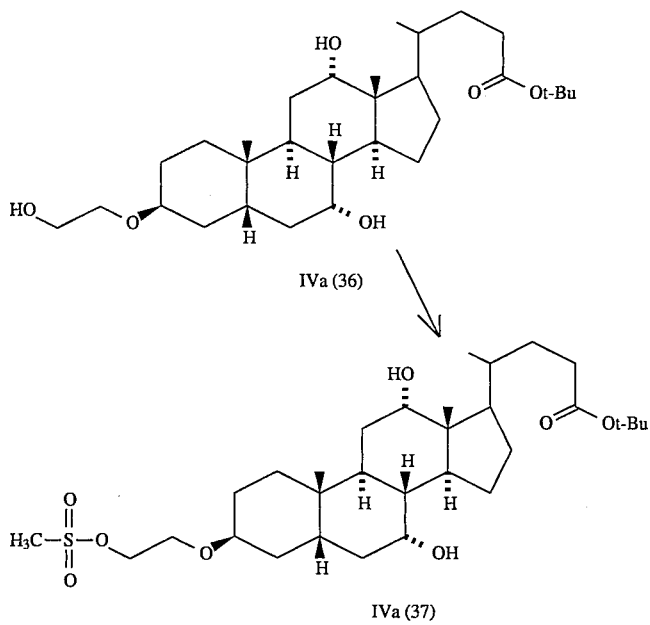

2.1 g (18.3 mmol) of methanesulfonyl chloride are added dropwise at 0° C. to 8.3 g (16.3 mmol) of IVa (36) in 50 ml of pyridine. The mixture is stirred at 0° C. for 15 minutes and at room temperature for 1 hour. The reaction mixture is poured into 100 ml of water and extracted 3 times with ethyl acetate. Drying of the combined organic phases (MgSO$_4$), removal of the solvent and chromatography on silica gel (ethyl acetate/cyclohexane 3:1) gives 8.6 g (14.7 mmol, 90%) of IVa (37).

$C_{31}H_{54}O_8S$ (586), MS (FAB, 3-NBA, LiI): 593 (M+Li$^+$).

EXAMPLE 30

8.4 g (14.3 mmol) of IVa (37) are stirred at 70° C. for 2 hours with 1.0 g (15.4 mmol) of sodium azide in 100 ml of dry DMSO. The reaction mixture is poured into water and extracted 3 times with ethyl acetate. The combined organic phases are dried (MgSO$_4$) and evaporated. The residue is taken up in toluene and evaporated again (2 times). Yield 7.6 g (quant.) of IVa (38). The azide is employed without further purification for the next step.

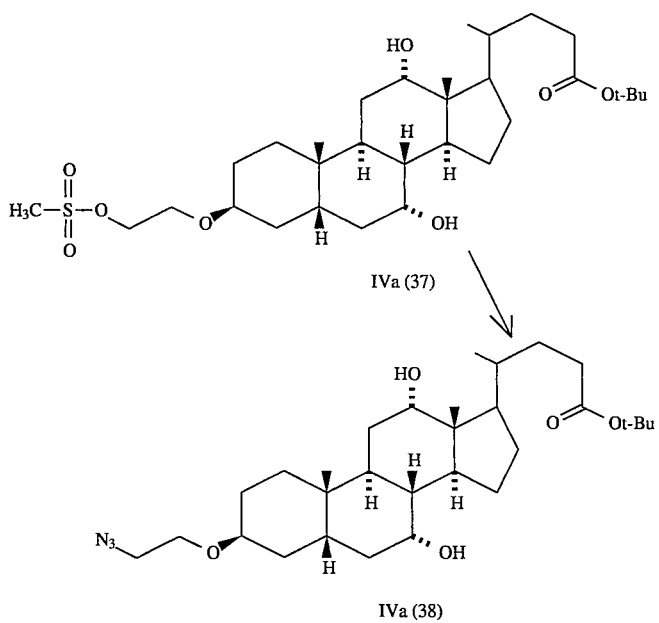

EXAMPLE 31

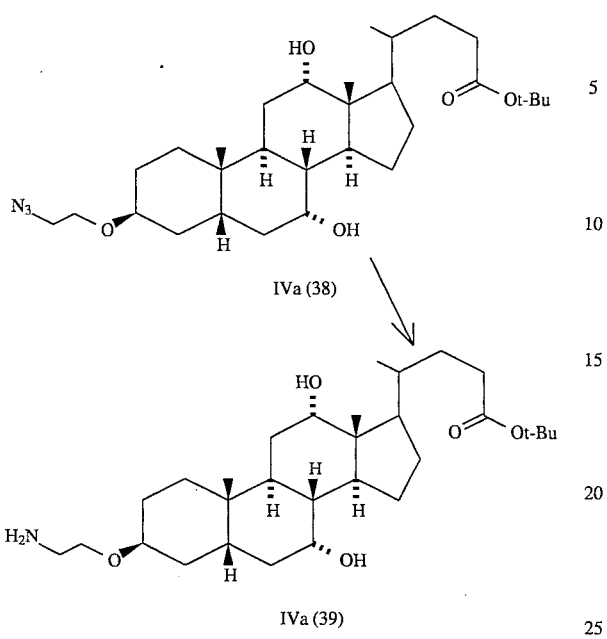

7.6 g (14.2 mmol) of IVa (38) are hydrogenated at room temperature under normal pressure in the presence of 5 g of Pd/C (10%) in 200 ml of ethyl acetate. The catalyst is filtered off and the filtrate is evaporated. Chromatography on silica gel (ethyl acetate/methanol/triethylamine 5:1:1) gives 5.0 g (9.85 mmol, 69%) of IVa (39).

$C_{30}H_{53}NO_3$ (507), MS (FAB, 3-NBA, LiI): 514 (M+Li$^+$).

EXAMPLE 32

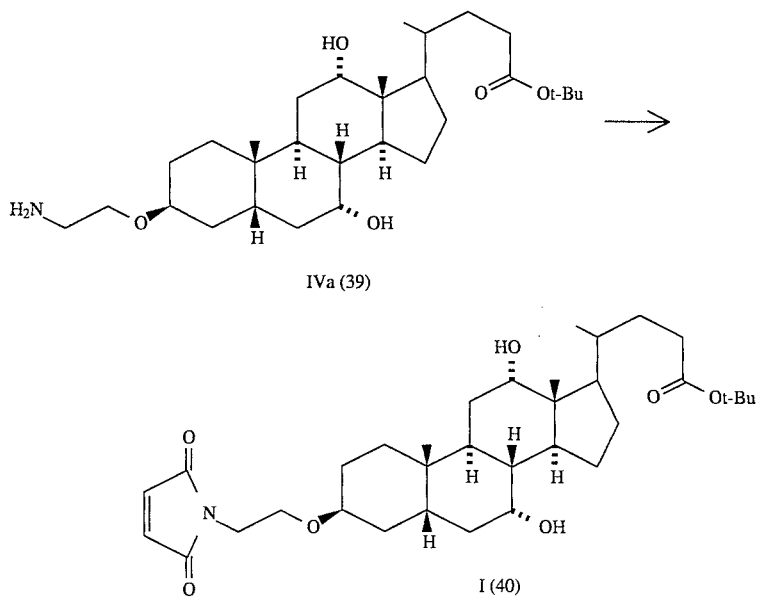

2.0 g (3.94 mmol) of IVa (39) and 570 mg (5.9 mmol) of maleic anhydride are dissolved in 10 ml of acetic acid and heated under reflux for 2 hours. After stripping off the solvent, the residue is chromatographed on silica gel (ethyl acetate/methanol/triethylamine 10:2:1). 1.0 g (1.7 mmol, 43%) of I (40) is obtained.

EXAMPLE 33

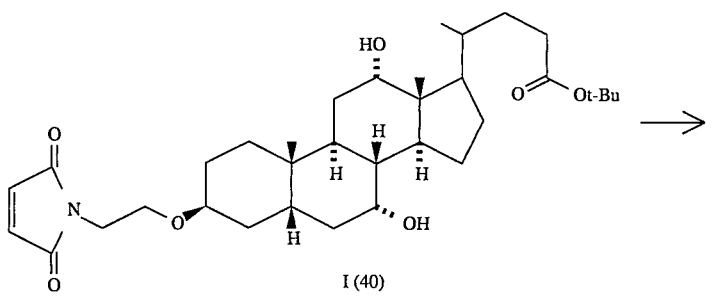

850 mg (1.45 mmol) of I (40) are dissolved in 20 ml of dichloromethane. 20 ml of trifluoroacetic acid are slowly added dropwise at 0° C. After 1.5 hours at 0° C., the mixture is stirred for a further 1 hour at room temperature. It is then concentrated in vacuo. 20 ml of toluene are added and the mixture is again concentrated. Chromatography on silica gel (chloroform/methanol 92:8) gives 380 mg (0.72 mmol, 49%) of I (41).

$C_{30}H_{45}NO_7$ (531), MS (FAB, 3-NBA, LiCl): 538 (M+Li$^+$).

EXAMPLE 34

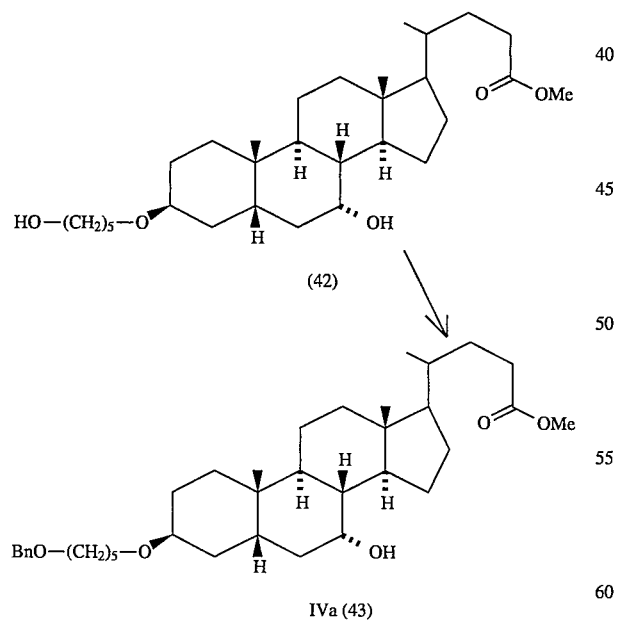

50 g (101.5 mmol) of (42) (EP-A-0,417,725) and 60 g (350 mmol) of benzyl bromide are stirred at 100° C. for 4 hours in 300 ml of N-ethyldiisopropylamine. After cooling, the reaction mixture is poured into 2 l of 2M sulfuric acid and extracted 3 times with ethyl acetate. The combined organic phases are extracted by shaking with aqueous NaHCO$_3$ solution, dried over MgSO$_4$ and evaporated in vacuo. Chromatography on silica gel (cyclohexane/ethyl acetate 6:4) gives 18.3 g (31.5 mmol, 31%) of IVa (43).

$C_{37}H_{58}O_5$ (582), MS (FAB, 3-NBA, LiCl): 589 (M+Li$^+$).

EXAMPLE 35

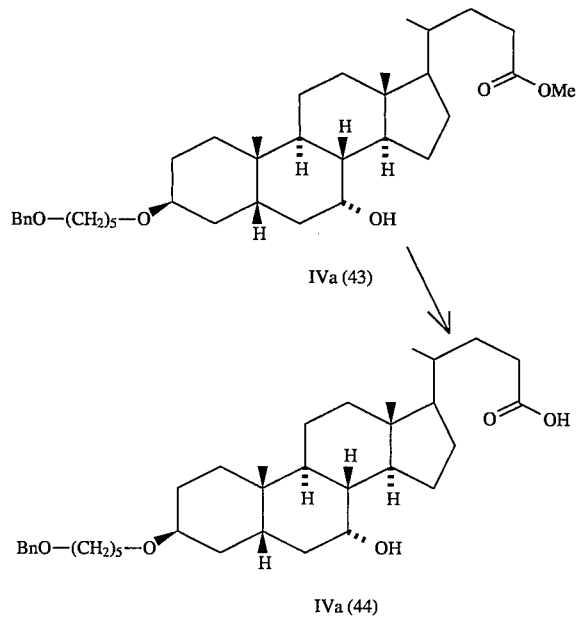

Starting from 18.0 g (30.9 mmol) of compound IVa (43), 16.0 g (28.1 mmol, 91%) of IVa (44) are prepared analogously to Example 26.

$C_{36}H_{56}O_5$ (568), MS (FAB, 3-NBA, LiCl): 575 (M+Li$^+$).

EXAMPLE 36

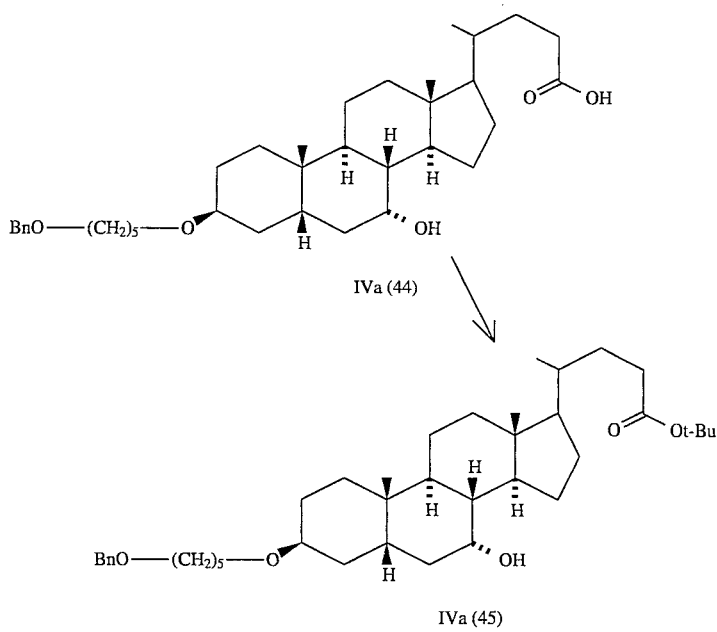

Starting from 16.0 g (28.1 mmol) of IVa (44), 8.5 g (13.6 mmol, 48%) of IVa (45) are prepared analogously to Example 27.

$C_{40}H_{64}O_5$ (624), MS (FAB, 3-NBA, LiCl): 631 (M+Li$^+$).

EXAMPLE 37

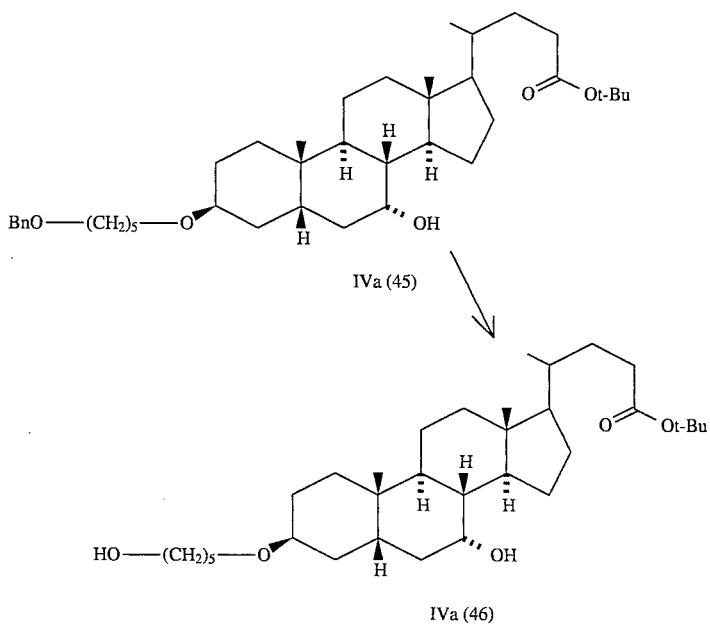

8.1 g (12.96 mol) of IVa (45) are hydrogenated at room temperature under normal pressure in the presence of 1 g of Pd/C (10%) in 250 ml of ethyl acetate. After completion of the reaction, the catalyst is filtered off and the filtrate is concentrated. 6.8 g (12.7 mmol 98%) of IVa (46) are obtained.

$C_{33}H_{58}O_5$ (534), MS (FAB, 3-NBA, LiCl): 541 (M+Li$^+$).

EXAMPLE 38
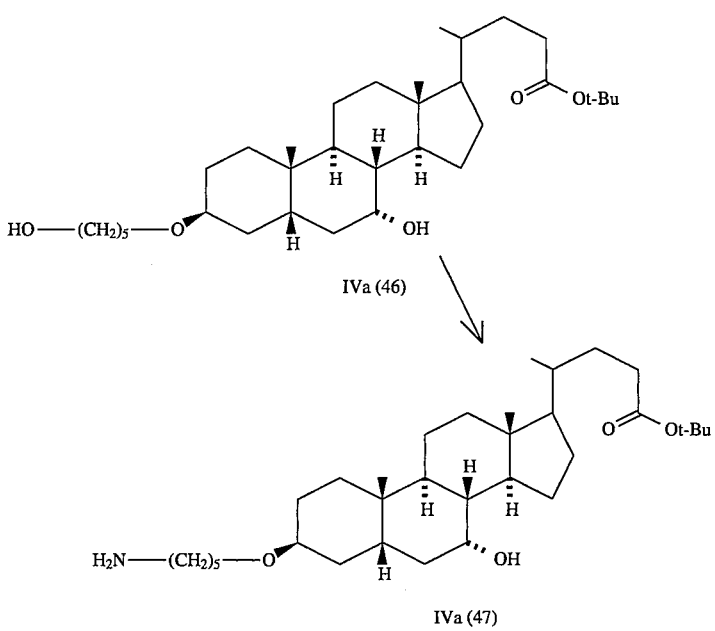
Starting from compound IVa (46), the compound IVa (47) is prepared in analogy to Examples 29–31.
$C_{33}H_{59}NO_4$ (533), MS (FAB,3-NBA, LiCl): 540 (M+Li$^+$).
EXAMPLE 39
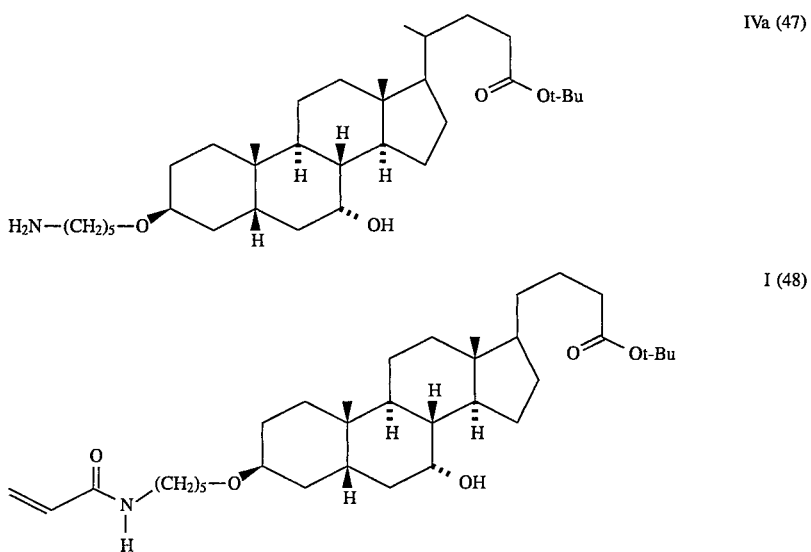
Starting from 1.8 g (3.37 mmol) of IVa (47), 1.2 g (2.04 mmol, 61%) of I (48) are obtained analogously to Example 24.
$C_{36}H_{61}NO_5$ (587), MS (FAB, 3-NBA, LiCl): 694 (M+Li$^+$).

EXAMPLE 40

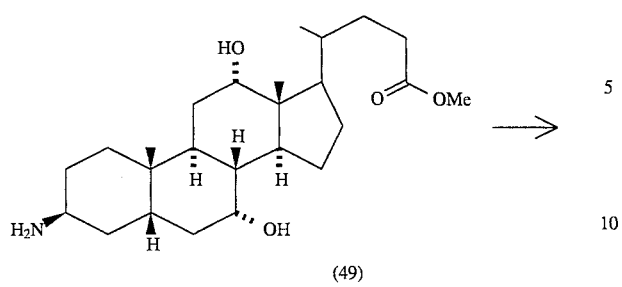

(49)

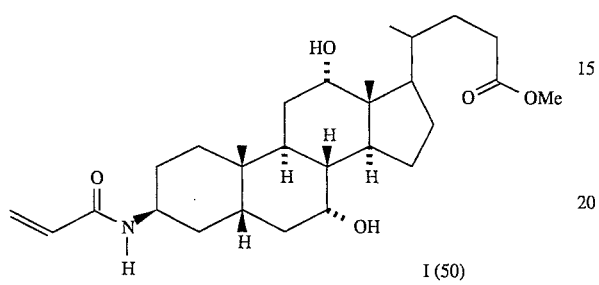

I (50)

Starting from 3.5 g (8.30 mmol) of (49) (EP-A-0,417, 725), 2.4 g (5.05 mmol, 61%) of I (50) are prepared analogously to Example 24.

$C_{28}H_{45}NO_5$ (475), MS, (FAB, 3-NBA, LiCl): 482 (M+Li$^+$).

EXAMPLE 41

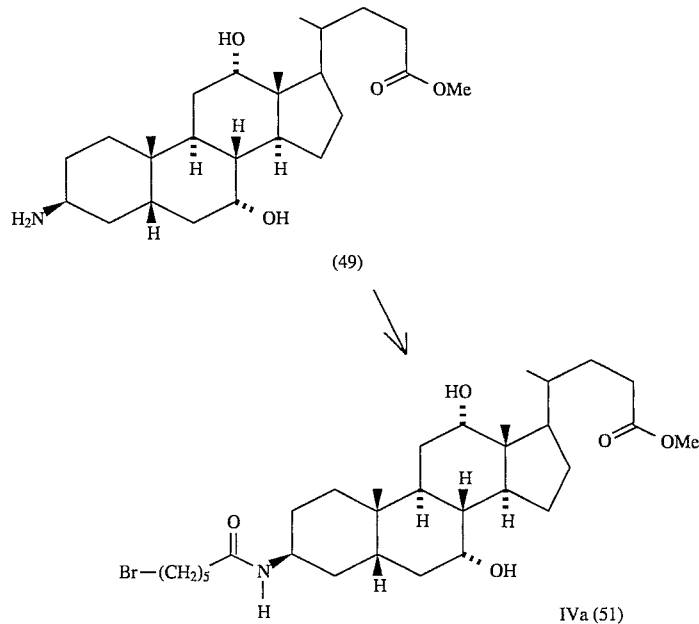

0.8 ml (5.26 mmol) of bromohexanoyl chloride are added dropwise at 0° C. to a solution of 2.0 g (4.74 mmol) of compound (49) and 0.8 mmol (5.74 mmol) of triethylamine in 50 ml of dichlormethane. After 10 min. at 0° C., the mixture is stirred for a further 1 hour at room temperature. For working up, it is poured into water, and the organic phase is washed again with water, then dried over sodium sulfate and concentrated in vacuo. After chromatography (ethyl acetate/cyclohexane 4:1), 1.36 g (2.27 mmol 48%) of IVa (51) are obtained.

$C_{31}H_{52}BrNO_5$ (597,599), MS (FAB, 3-NBA, LiCl): 604, 606 (M+Li$^+$).

EXAMPLE 42

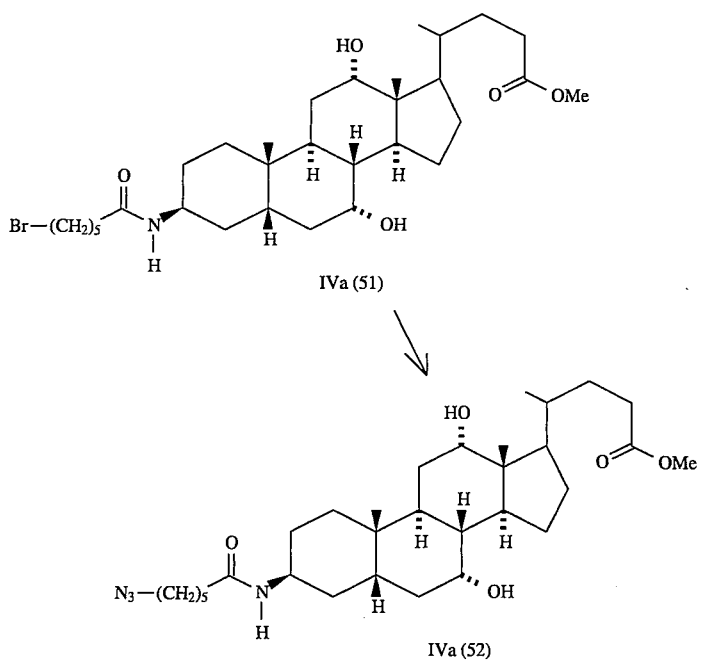

5.7 g (9.52 mmol) of IVa (51) and 1.0 g (15.4 mmol) of NaN$_3$ are stirred at 70° C. for 4 hours in 100 ml of dimethylformamide. After cooling, the mixture is poured into water and extracted 3 times with ether. The organic phases are dried over sodium sulfate and concentrated. After chromatography (ethyl acetate) 4.6 g (8.20 mmol, 86%) of IVa (52) are obtained.

C$_{30}$H$_{52}$N$_4$O$_5$ (560), MS (FAB, 3-NBA, LiCl): 567 (M+Li$^+$).

EXAMPLE 43

4.55 g (8.11 mmol) of compound IVa (52) are dissolved in 200 ml of ethyl acetate and hydrogenated at room temperature under normal pressure in the presence of 500 mg of Pd/C (10%). After completion of the reaction, the catalyst is filtered off and the filtrate is concentrated. After chromatography (chloroform/methanol 8:2), 2.7 g (5.05 mmol, 62%) of IVa (53) are obtained. C$_{31}$H$_{54}$N$_2$O$_5$ (534), MS (FAB, 3-NBA, LiCl): 541 (M+Li$^+$).

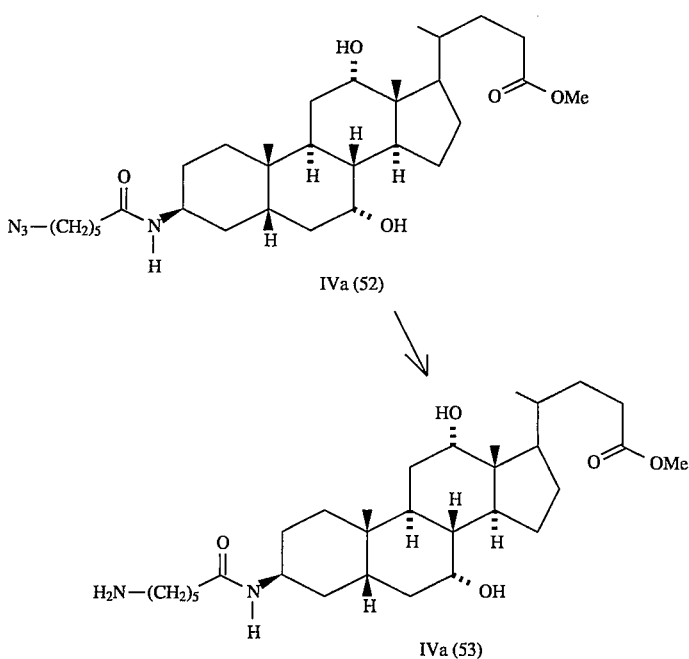

EXAMPLE 44

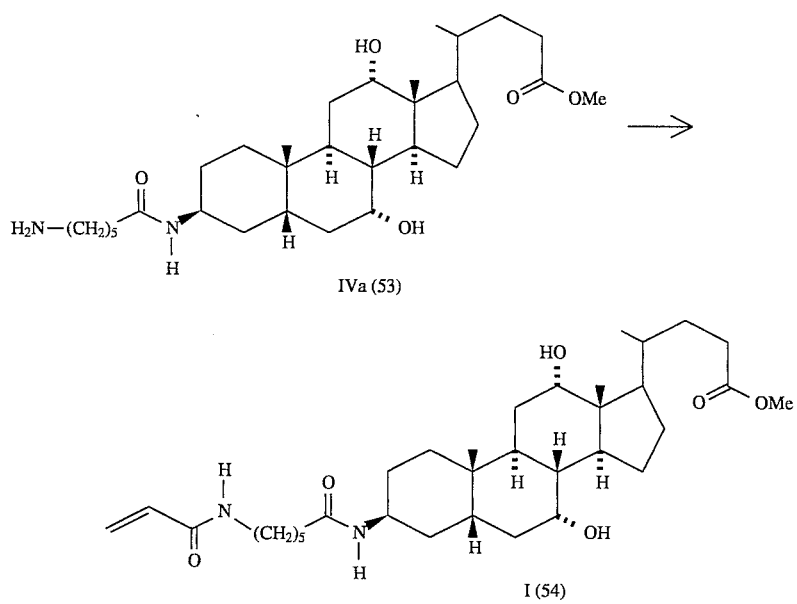

Starting from 2.6 g (4.86 mmol) of IVa (53), 1.4 g (2.38 mmol, 49%) of I (54) are prepared analogously to Example 24.

$C_{34}H_{56}N_2O_6$ (588), MS (FAB, 3-NBA, LiCl): 595 (M+Li$^+$).

EXAMPLE 45

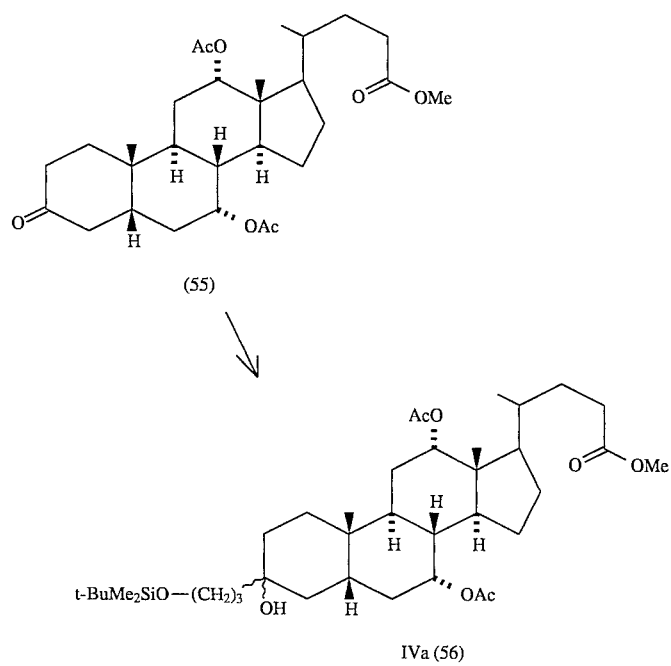

A Grignard solution prepared from 9.4 g (37.1 mmol) of 1-bromo-3-t-butyldimethylsilyloxypropane and 1.0 g (42 mmol) of magnesium is added dropwise at room temperature to a solution of 8.0 g (15.85 mmol) of compound (55) (Helv. chim. Acta 28, 344, 1945) in 100 ml of THF. The mixture is then heated under reflux for 2 hours. For working up, it is poured into aqueous NH$_4$Cl solution (10%) and extracted 3 times using ethyl acetate. The combined organic phases are dried over MgSO$_4$ and evaporated in vacuo. By chromatography of the crude product on silica gel (cyclohexane/ethyl acetate 4:1, then 2:1), 3.6 g (5.30 mmol, 44%) of IVa (56) are obtained first as the main product and 1.2 g (1.77 mmol, 11%) of by-product are obtained second.

Main product: $C_{38}H_{66}O_8Si$ (678), MS (FAB, 3-NBA, LiCl): 685 (M+Li$^+$).

By-product: $C_{38}H_{66}O_8Si$ (678), MS (FAB, 3-NBA, LiCl): 685 (M+Li$^+$).

EXAMPLE 46

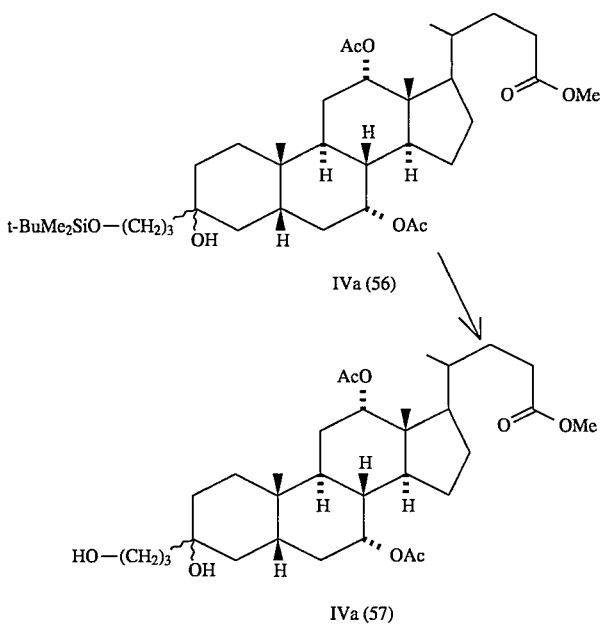

3.4 g (5.01 mmol) of compound IVa (56) are stirred for 1 hour at room temperature with 1.75 g (5.55 mmol) of tetrabutylammonium fluoride trihydrate in 100 ml of tetrahydrofuran. For working up, the mixture is poured into water and extracted 3 times with ethyl acetate. After drying the organic phase over MgSO$_4$, the mixture is evaporated in vacuo. Chromatography of the residue on silica gel (cyclohexane/ethyl acetate 1:1) gives 2.1 g (3.72 mmol, 74%) of IVa (57).

$C_{32}H_{52}O_8$ (564), MS (FAB, 3-NBA, LiCl): 571 (M+Li$^+$).

EXAMPLE 47

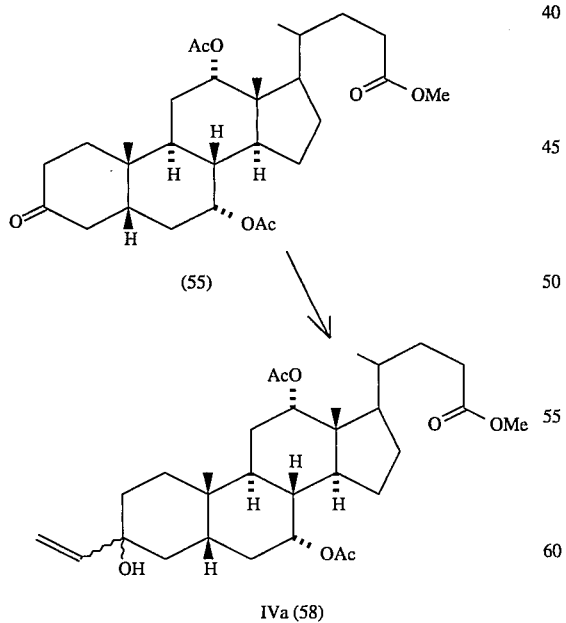

A 1M solution of vinylmagnesium bromide in tetrahydrofuran is added dropwise at –70° C. to a solution of 10.0 g (19.81 mmol) of compound (55) in 300 ml of tetrahydrofuran. The mixture is stirred for a further 1 hour at –70° C. After completion of the reaction, 50 ml of NH$_4$Cl solution (10%) are added and the mixture is warmed to room temperature. Water is additionally added and the mixture is extracted 3 times with ethyl acetate. After drying of the combined organic phases over MgSO$_4$, they are evaporated in vacuo. The diastereomer mixture obtained is chromatographed on silica gel (cyclohexane/ethyl acetate 2:1). The main product IVa (58) is obtained as the first fraction, 5.7 g (10.70 mmol, 54%) and the by-product is obtained as the second fraction, 6.3 g (2.4 mmol, 12%).

Main product: $C_{31}H_{48}O_7$ (532), MS (FAB, 3-NBA, LiCl): 539 (M+Li$^+$)

By-product: $C_{31}H_{48}O_7$ (532), MS (FAB, 3-NBA, LiCl): 539 (M+Li$^+$).

EXAMPLE 48

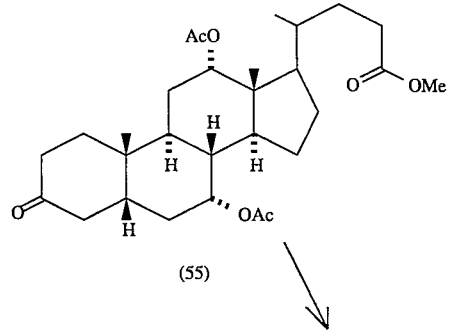

81
-continued

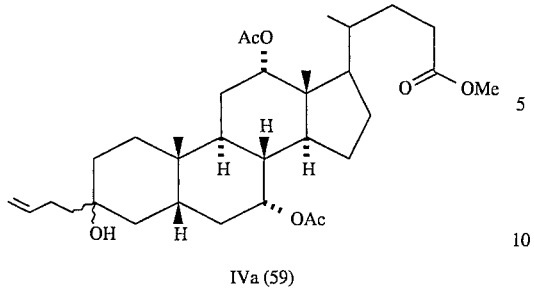

IVa (59)

A Grignard solution is prepared in 300 ml of THF from 10.2 ml (110 mmol) of 4-bromo-1-butene and 2.4 g (100 mmol) of magnesium. At room temperature, 20 g (39.6 mmol) of compound (55) are added dropwise in 100 ml of THF. After stirring at room temperature for 3 hours, 250 ml of NH$_4$Cl solution are added and the mixture is extracted 3 times using ethyl acetate. The combined organic phases are dried over Na$_2$SO$_4$ and concentrated. Chromatography on silica gel (cyclohexane/ethyl acetate 4:1) gives 13.5 g (24.1 mmol, 61%) of IVa (59) as the main product.

$C_{33}H_{52}O_7$ (560) MS (FAB, 3-NBA, LiCl): 567 (M+Li$^+$).

82
EXAMPLE 49

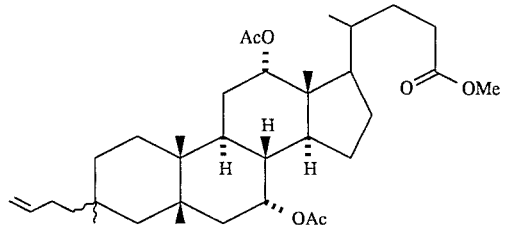

IVa (59)

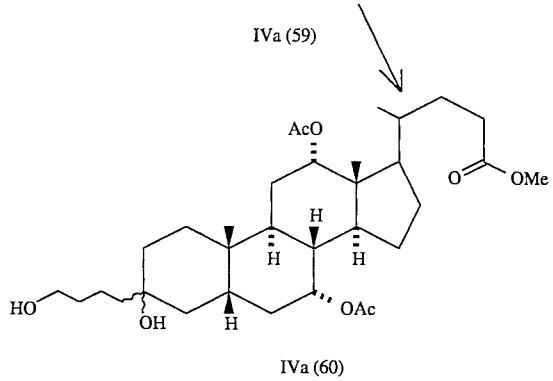

IVa (60)

4.0 ml of a 1M solution of borane in tetrahydrofuran are added dropwise at −30° C. to 1.0 g (1.78 mmol) of IVa (59) in 30 ml of tetrahydrofuran. After 2 hours at −30° C. and 8 hours at room temperature, the mixture is cooled to 0° C., 2.0 ml of 2M sodium hydroxide and then 0.68 ml of 36% strength H$_2$O$_2$ are added and the mixture is stirred for a further 30 min at room temperature. For working up, it is treated with saturated sodium chloride solution and extracted 3 times using ethyl acetate. The combined organic phases are dried over MgSO$_4$ and concentrated. Chromatography on silica gel (ethyl acetate) gives 0.5 g (0.86 mmol, 48%) of IVa (60).

$C_{33}H_{54}O_8$ (578), MS (FAB, 3-NBA, LiCl): 585 (M+Li$^+$).

EXAMPLE 50

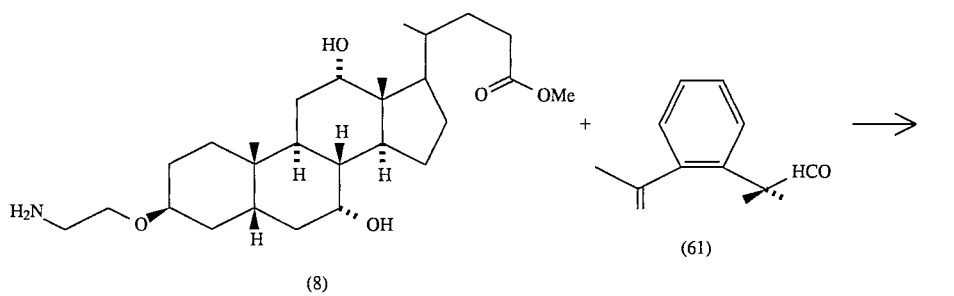

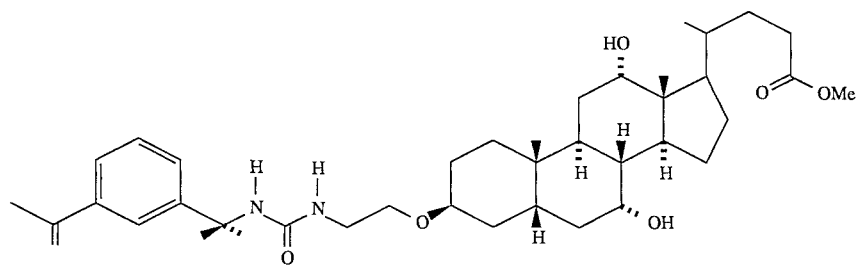

I (62)

65

700 mg (3.48 mmol) of (61) (1-(1-isocyanato-1-methylethyl)-4-(1-methylethenyl)benzene) in 5 ml of chloroform are slowly added dropwise at 0° C. to a solution of 1.57 g (3.37 mmol) of (8) in 50 ml of chloroform. The mixture is stirred at 0° C. for 1 hour and at room temperature for 15 min. For working up, it is poured into water and extracted 3 times using chloroform. The combined organic phases are dried over MgSO$_4$ and concentrated. Chromatography on silica gel (chloroform/methanol 92.5:7.5) gives 1.92 g (2.88 mmol, 85%) of I (62)

$C_{40}H_{62}N_2O_6$ (666), MS (FAB, 3-NBA, LiCl): 673 (M+Li$^+$).

EXAMPLE 51

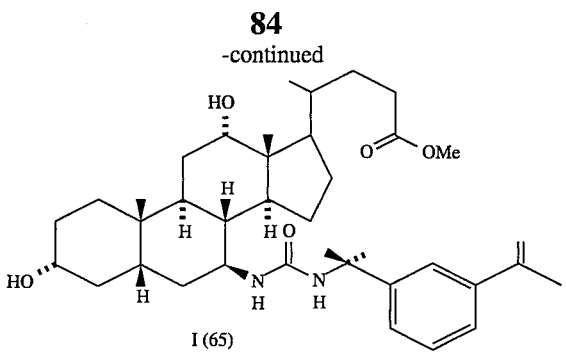

I (65)

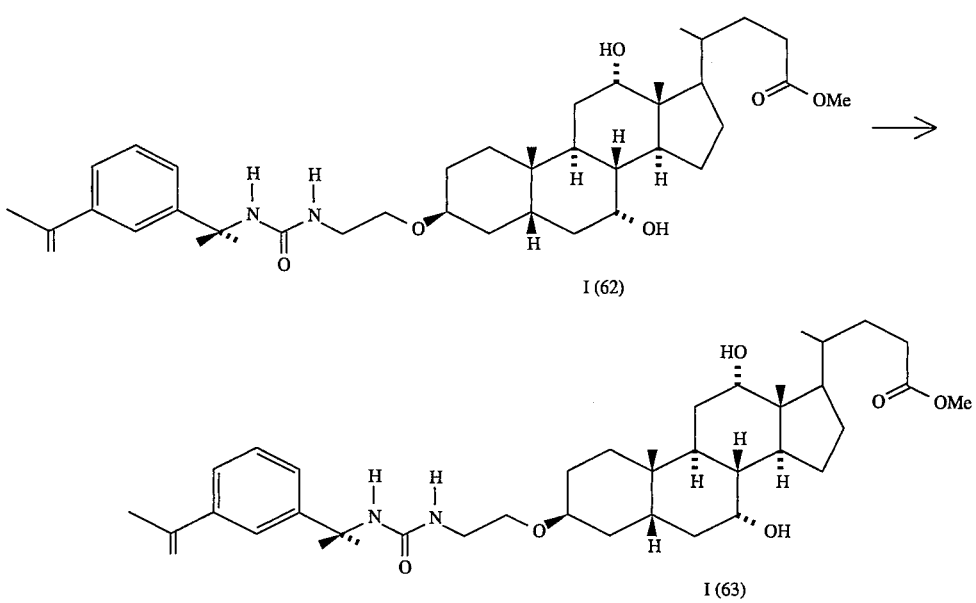

I (62)

I (63)

380 mg (0.57 mmol) of I (62) are dissolved in 20 ml of ethanol and treated with 6 ml of 1M aqueous NaOH. After stirring at room temperature for 4 hours, 100 ml of water are added. The ethanol is stripped off in a rotary evaporator. The pH is brought to 1 using 2N HCl and the mixture is extracted 3 times using chloroform. The combined organic phases are dried over MgSO$_4$ and evaporated in vacuo. Chromatography on silica gel gives 300 mg (0.46 mmol, 81%) of I (63).

$C_{39}H_{60}N_2O_6$ (652), MS (FAB, 3-NBA, LiCl): 659 (M+Li$^+$).

EXAMPLE 52

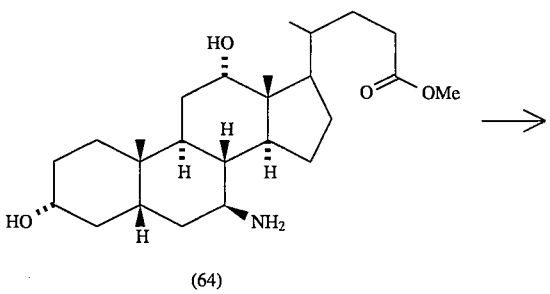

(64)

Starting from 1.5 g (3.56 mmol) of (64) (Bull. Chim. Soc. France 877, 1949; J. Chem. Soc. 2164,1949) and 750 mg (3.73 mmol) of (61), 1.39 g (2.23 mmol, 63%) of I (65) are prepared by the process described for Example 50.

$C_{38}H_{58}N_2O_5$ (622), MS (FAB, 3-NBA, LiCl): 629 (M+Li$^+$).

We claim:

1. An ethylenically unsaturated bile acid derivative of the formula I in which

G is a compound of formula III having rings a and b,

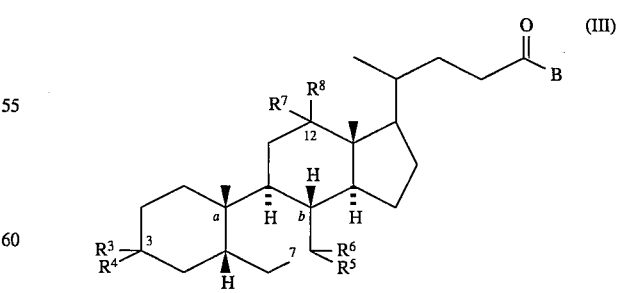

in which $R^5$ to $R^8$ independently of one another are hydrogen, OH, NH$_2$ or an OH group protected by an OH protective group, $R^3$ and $R^4$ independently of one another are hydrogen, NH$_2$ or an OH group protected by an OH protective group, and one of the radicals $R^3$ or $R^4$, is a bond to the group X, where this bond starts from position 3($R^3$ or $R^4$) and the position 7($R^5$ or $R^6$) carries an OH group or a protected OH group, B is —O-alkali metal, —O-alkaline earth metal, —O—($C_1$–$C_{12}$)-alkyl, —O-allyl or —O-benzyl, where a resultant ester group

is an ester optionally hydrolyzed by acid or by base, and G is bonded via ring a or b to the group X wherein, X is a bridge group of formula II $$(Y)_o—(Z)_p \qquad (II)$$

in which

Y is adjacent to G and is —O—, —NR'—, or

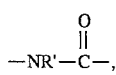

Z is ($C_1$–$C_{12}$)-alkylene or ($C_7$–$C_{13}$)-aralkylene, where individual methylene groups in the alkylene chain of the alkylene or aralkylene can be replaced by groups selected from the group consisting of —O—, —NR'—,

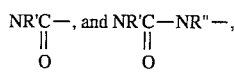

o and p independently of one another are zero or one, where o and p are not simultaneously zero, and A is

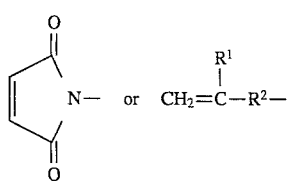

where $R^1$ is hydrogen or $CH_3$ and $R^2$ is

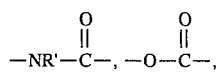

—O—, —NR'— or a single bond, where the carbonyl groups are adjacent to the C—C double bond, and R' and R" independently of one another are hydrogen or ($C_1$–$C_6$) alkyl.

2. A compound as claimed in claim 1, wherein p=zero, o=1, and Y is

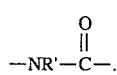

3. A compound as claimed in claim 1, wherein p=1, o=zero, and Z is ($C_1$–$C_{12}$)-alkylene, where 1–3 methylene groups are replaced by

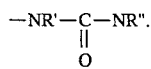

4. A compound as claimed in claim 1, wherein p=1, o=1, Y is —O—, and Z is ($C_1$–$C_{12}$)-alkylene or ($C_7$–$C_{13}$)-aralkylene, where 1 or 2 methylene groups are replaced by

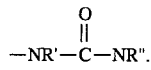

5. A compound as claimed in claim 1, wherein A is

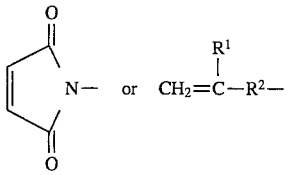

where $R^1$ is hydrogen or $CH_3$ and $R^2$ is

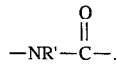

6. A compound as claimed in claim 1, wherein p=1, o=zero, and Z is ($C_7$–$C_{13}$)-aralkylene, where 1–3 methylene groups in the alkylene chain are replaced by

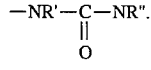

7. A compound as claimed in claim 1, wherein p=1, o=1, Y is —O—, and Z is ($C_1$–$C_{12}$)-alkylene or ($C_7$–$C_{13}$)- arylalkylene, where 1 or 2 methylene groups are replaced by
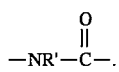
8. A compound as claimed in claim 1, wherein
A is
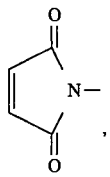
9. A compound as claimed in claim 1, wherein
A is
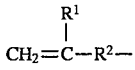
where
R$^1$ is hydrogen or CH$_3$ and
R$^2$ is
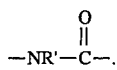
* * * * *